United States Patent
Krill et al.

(10) Patent No.: US 11,661,395 B2
(45) Date of Patent: May 30, 2023

(54) REACTOR AND PROCESS FOR PRODUCING ALKYL METHACRYLATES

(71) Applicant: Röhm GmbH, Darmstadt (DE)

(72) Inventors: Steffen Krill, Muehltal (DE); Andreas Rühling, Darmstadt (DE); Belaid Ait Aissa, Darmstadt (DE)

(73) Assignee: Röhm GmbH, Darmstadt (DE)

( * ) Notice: Subject to any disclaimer, the term of this patent is extended or adjusted under 35 U.S.C. 154(b) by 0 days.

(21) Appl. No.: 17/664,924

(22) Filed: May 25, 2022

(65) Prior Publication Data

US 2022/0380293 A1 Dec. 1, 2022

(30) Foreign Application Priority Data

May 28, 2021 (EP) .................................... 21176518

(51) Int. Cl.
  *C07C 67/42* (2006.01)
  *B01J 19/18* (2006.01)
  *B01J 35/02* (2006.01)

(52) U.S. Cl.
  CPC ........... *C07C 67/42* (2013.01); *B01J 19/1856* (2013.01); *B01J 35/026* (2013.01); *B01J 2219/00481* (2013.01)

(58) Field of Classification Search
  CPC ......... C07C 67/42; C07C 67/39; C07C 69/54; B01J 19/1856; B01J 35/026; B01J 2219/00481; B01J 35/023
  See application file for complete search history.

(56) References Cited

U.S. PATENT DOCUMENTS

| | | | |
|---|---|---|---|
| 5,288,673 | A | 2/1994 | Behrmann et al. |
| 5,417,930 | A | 5/1995 | McDonald, Jr. et al. |
| 5,969,178 | A | 10/1999 | Okamoto et al. |
| 6,040,472 | A | 3/2000 | Yamamatsu et al. |
| 7,012,039 | B2 | 3/2006 | Watanabe et al. |

(Continued)

FOREIGN PATENT DOCUMENTS

| | | |
|---|---|---|
| CN | 101314120 | 12/2008 |
| CN | 104418309 | 3/2015 |

(Continued)

OTHER PUBLICATIONS

Acrivos et al. "Enhanced sedimentation in settling tanks with inclined walls", Journal Fluid. Mech., vol. 92, Part 3, 1979, 99, pp. 435-457.

(Continued)

*Primary Examiner* — Jafar F Parsa
(74) *Attorney, Agent, or Firm* — Grüneberg and Myers, PLLC

(57) ABSTRACT

A process produces methyl methacrylate by direct oxidative esterification of methacrolein. Methyl methacrylate is used in large amounts for producing polymers and copolymers with other polymerizable compounds. An optimized workup of the reactor discharge from the oxidative esterification of methacrolein allows for co-discharged fine catalyst particles to be very efficiently separated and optionally removed or recycled. In addition, this process can reduce the formation of byproducts in extended continuous operation compared to known variant. A reactor system contains stirrer configurations which allow virtually abrasion-free operation and thus a catalyst on-stream time of several years.

20 Claims, 9 Drawing Sheets

(56) References Cited

U.S. PATENT DOCUMENTS

| | | |
|---|---|---|
| 8,450,235 B2 | 5/2013 | Suzuki et al. |
| 9,617,199 B2 | 4/2017 | Krill et al. |
| 9,890,105 B2 | 2/2018 | Krill et al. |
| 9,963,417 B2 | 5/2018 | Krill et al. |
| 10,232,353 B2 | 3/2019 | Lygin et al. |
| 10,596,539 B2 | 3/2020 | Lygin et al. |
| 11,124,471 B2 | 9/2021 | Lygin et al. |
| 11,299,449 B2 | 4/2022 | Krill et al. |
| 2013/0172599 A1 | 7/2013 | Suzuki et al. |
| 2016/0251301 A1 | 9/2016 | Krill et al. |
| 2016/0280628 A1 | 9/2016 | Krill et al. |
| 2019/0099731 A1 | 4/2019 | Lygin et al. |
| 2021/0032386 A1 | 2/2021 | Krill et al. |
| 2021/0047259 A1 | 2/2021 | Lygin et al. |
| 2021/0269385 A1 | 9/2021 | Krill et al. |
| 2022/0204436 A1 | 6/2022 | Krill et al. |

FOREIGN PATENT DOCUMENTS

| | | |
|---|---|---|
| EP | 1 393 800 | 3/2004 |
| EP | 2 177 267 | 4/2010 |
| EP | 2 210 664 | 7/2010 |
| EP | 3 235 560 | 10/2017 |
| EP | 3 244 996 | 11/2017 |
| JP | H09-248403 | 9/1997 |
| JP | H10-94705 | 4/1998 |
| WO | 2012/152600 | 11/2012 |
| WO | 2014/170223 | 10/2014 |
| WO | 2016/113106 | 7/2016 |

OTHER PUBLICATIONS

U.S. Appl. No. 16/637,575, filed Feb. 7, 2020, 2021/0032386, Krill et al.
U.S. Appl. No. 17/597,345, filed Jan. 4, 2022, 2022/0204436, Krill et al.
U.S. Appl. No. 17/753,245, filed Feb. 24, 2022, Krill et al.
U.S. Appl. No. 17/804,057, filed May 25, 2022, Krill et al.

REACTOR AND PROCESS FOR PRODUCING ALKYL METHACRYLATES

CROSS-REFERENCE TO RELATED APPLICATIONS

This application claims priority to European Application No. 21176518, filed on May 28, 2021, the content of which is hereby incorporated by reference in its entirety.

BACKGROUND OF THE INVENTION

Field of the Invention

The present invention relates to a process for producing methyl methacrylate by direct oxidative esterification of methacrolein. Methyl methacrylate is used in large amounts for producing polymers and copolymers with other polymerizable compounds. In addition, methyl methacrylate is an important synthesis unit for a variety of specialty esters based on methacrylic acid (MAA) which can be produced by transesterification with the appropriate alcohol. There is consequently a great interest in very simple, economic and environmentally friendly processes for producing this starting material.

The present invention especially relates to a suitable and optimized reactor system and an optimized workup of the reactor discharge from the oxidative esterification of methacrolein by means of which co-discharged fine catalyst particles may be very efficiently separated and optionally removed or recycled. In addition, this novel process can reduce the formation of byproducts in extended continuous operation compared to known variants.

The reaction system comprises a stirrer system which is configured such that it reduces the abrasion of the catalyst particles to a minimum and ensures the mechanical intactness of the suspension catalyst in long-term continuous operation. At the same time a high gas dispersion, an ideal gas distribution and finally a high space-time yield is ensured.

The invention especially describes a system for separation and recirculation of the reaction matrix and suspended catalyst, wherein the triphasic reaction mixture is permanently degassed and recirculated as a biphasic mixture and simultaneously through sedimentation in an inclined settler the biphasic reaction mixture is converted into a largely monophasic mixture which is continuously removed from the reactor and thus allows trouble-free workup of the desired target products and simultaneously noble metal-containing particles exiting the reactor are collected in a filter system, optionally recycled and the noble metal recovered.

Description of Related Art

Methyl methacrylate (MMA) is currently produced by a variety of processes proceeding from $C_2$, $C_3$ or $C_4$ synthesis units. The general prior art is described substantially in current reviews and overview articles.

a.) Nexant, CHEMSYSTEMS PERP PROGRAM, Methyl Methacrylate PERP 08/09-7 March 2010, b.) R. J. Chang, S. Naqvi, IHS Chemical PEP Report Methyl Methacrylate (MMA) Process Summary 2014-05.

c.) "Trends and Future of Monomer-MMA Technologies", K. Nagai & T. Ui, Sumitomo Chemical Co., Ltd.; Basic Chemicals Research Laboratory, www.sumitomochem.co.jp/english/rd/report/theses/docs/20040200_30a.pdf, 2005.

d.) "Viele Wege führen zum Methacrylsäuremethylester" [Many routes lead to methyl methacrylate], S. Krill, A. Ruehling, H. Offermanns, Chem. Unserer Zeit, 2019, 53; ©2019 Wiley-VCH Verlag GmbH & Co. KGaA, Weinheim In one of these processes MMA is obtained by gas-phase oxidation of isobutylene or tert-butanol with atmospheric oxygen over the heterogeneous catalyst to afford methacrolein and subsequent oxidative esterification of methacrolein using methanol. In this altogether two-stage process the (meth)acrolein obtained by gas phase oxidation over a fixed bed catalyst is condensed, purified and in the second stage reacted with methanol in the liquid phase by direct oxidative esterification (DOE process) to afford MMA. This process, developed by ASAHI, is described, inter alia, in publications U.S. Pat. Nos. 5,969,178 and 7,012,039. A particular disadvantage of this process is a very high energy requirement. In a development of the process the methacrolein is obtained from propanal and formaldehyde in the first stage. Such a process is described in WO 2014/170223.

The catalytic oxidative esterification of aldehydes for production of carboxylic esters is described extensively in the prior art. For example, it is possible in this way to produce methyl methacrylate very efficiently from methacrolein (MAL) and methanol. However, for this reaction step all of the catalysts known from the prior art exhibit a sensitivity especially to aqueous media in the case of prolonged on-stream times. This especially results in a measurable discharge of metal compounds, support components and active metal components of the catalyst.

A characteristic of the processes described in U.S. Pat. Nos. 5,969,178 and 7,012,039 which comprise as a central step the direct oxidative esterification of methacrolein with methanol to afford MMA is the use of a heterogeneous, supported Pd—Pb-based catalyst which features especially an excellent longevity and very high MMA selectivities of up to 93%. The pulverulent catalyst is employed in a slurry reactor, i.e. in a triphasic reaction system, consisting of a liquid reaction matrix, the suspended catalyst and the oxygen-containing gas, in the simplest case air. As advantageous as the high selectivities of the DOE process make the process seem, there was nevertheless a considerable need for development with regard to the employed catalyst which has a propensity for metal losses, and the present case so-called leaching of lead. These losses in the form of soluble lead ions entail considerable cost and complexity in the workup, particularly as the lead ions require precipitation as poorly soluble lead compounds, for example lead sulfate, and separation in the workup. Furthermore, a soluble lead compound must in this case be metered into the reactor to maintain catalyst activity. Separation of fine particles and control and prevention of abrasion of the pulverulent catalysts is not described and remains a problem, particularly as noble metal-containing fine particles and lead sulfate crystals appear to require separation together.

U.S. Pat. No. 6,040,472 describes alternative catalysts, but these lead only to inadequate activities and selectivities for MMA by comparison. In this case the catalysts are Pd/Pb-containing catalysts having a shell structure. The selectivities for MMA are reported to be up to 91%, and the space-time yield is reported to be up to 5.3 mol.

Some of the problems of lead leaching of the palladium-lead catalysts have been solved by finding novel catalysts containing gold as the active oxidation element and no lead as a dopant. A catalyst support is always used, often a complex mixture of different metal oxides with other element oxide or else polymeric support materials.

For example, EP 1 393 800 describes good activities and selectivities, but at the same time no information is given as to the lifetime of the catalysts. These catalysts are gold-containing catalysts, especially gold nanoparticles having an average diameter of less than 6 nm on a support. The selectivities for MMA at a content of 4.5% by weight of Au are reported to be up to 93%, and the space-time yield is reported to be up to 50.7 mol of MMA/kg cat.*h. The pH of the gold-containing solution in the catalyst production is in the range from 5 to 10, preferably between 6 and 9.

EP 2 177 267 and EP 2 210 664 describe nickel-containing catalysts with shell structure. Selectivity for MMA in the case of these catalysts is up to 97%. The space-time yield is described as 9.7 mol of MMA/kg cat.*h with a gold content in the catalyst of about 1% by weight.

US 2013/0172599, in turn, describes a silicon-containing material consisting of Si, Al and a basic third component, and also a metal having elevated acid resistance. This metal is Ni, Co, Zn or Fe. This material can be used as support for noble metal-containing catalysts. A preferred catalyst variant for the oxidative esterification of methacrolein to MMA includes an Au/NiO catalyst supported on $SiO_2$—$Al_2O_3$—MgO.

However, it is apparent from comparative example 2 that this catalyst loses activity with time. This is probably attributable to the adverse effect of water present in the reaction mixture.

Good results in terms of on-stream time, activity and selectivity are achieved with catalysts of later generations. For instance, EP 3 244 996 describes a gold-based catalyst which comprises not only gold but also a further metal/metal oxide in the outer shell. Such additionally present components may be for example cobalt or nickel or oxides thereof. The purpose thereof is to avoid sintering of the nanogold particles on the catalyst surface under long-term operation. Similarly to the alternatives described above, the support material of such catalysts may consist of mixed oxides, especially silicon, aluminium and magnesium and/or other non-noble metals.

Meanwhile a second catalyst generation has been developed which is based on a core-shell catalyst consisting of $NiO_x$ and gold and solves substantial disadvantages and problems of the original process. In contrast to the first catalyst generation, it was possible to significantly increase long-term stability and long-term activity. These new developments are described in S. Stahl and P. Alsters, "Liquid Phase Aerobic Oxidation Catalysis", publ. 17 Aug. 2016, Print ISBN 9783527337811, Wiley-VCH Verlag GmbH, see Ken Suzuki, pages 209-2018 or in U.S. Pat. No. 8,450,235. This document refers to the long catalyst lifetime of the catalyst systems.

What is to be provided is a suitable reactor system for meeting industrial requirements in addition to the demand for highly selective oxidation catalysts exhibiting long-term stability and chemical suitability of the catalyst system.

This is a great challenge for the performance of triphasic reactions in the simultaneous presence of a gaseous phase (oxygen-containing gas), a solid phase (the heterogeneous, insoluble catalyst) and the liquid phase (the reaction matrix containing reactants and products and also byproducts) because a multiplicity of requirements must be met, for example heat removal, avoidance of pH gradients, sufficient space-time yield, sufficient distribution of gas bubbles, control of the gas dispersion and coalescence of the gas bubbles, control of the solid gradient in the reactor, minimal abrasion by convection and many more.

To this end the prior art describes numerous reactor systems for performing such triphasic reactions in the presence of suspension catalysts.

A known variation of such reactors is that of reactors having an inner tube, a so-called "draft tube", which allow internal circulation. For instance, U.S. Pat. No. 5,288,673 describes the use of a slurry reactor with a draft tube for a Fischer-Tropsch synthesis for production of hydrocarbons from synthesis gas.

CN 104418309 describes a slurry reactor with a draft tube for hydrogen peroxide production in a heterogeneously catalysed hydrogenation reaction of anthraquinone. The catalyst concentration used is about 10 g/l (<0.01 kg/kg of mixture) and is thus relatively low. The flow direction in the draft tube from the bottom upward constantly conveys a high proportion of the catalyst back into the tube.

WO 2012/152600 describes an ammoxidation of cyclohexanone which is performed with a heterogeneous TS-1 catalyst as a triphasic reaction (gaseous-liquid-solid). Both the heat transfer and the mass transfer in this process can be distinctly improved when a cylindrical draft tube is used. The reactants are metered in here at different points. One metered addition is effected below the draft tube (here $NH_3$), one above the draft tube (here $H_2O$) and optionally a further metered addition from the side (here cyclohexanone for example). Filtration is effected with the aid of many candle filters having a high total area. These are positioned at the midpoint of the reactor height and at the outer edge of the draft tube. According to the description, the process can be performed without interruption and filter backwashing for 1 year. After one year, the filters then have to be cleaned.

There is no description of the use of slurry reactors with internal circulation for the reactions in which formation of deposits is possible, such as, more particularly, for reactions in which polymerizable substances, for example, are produced. U.S. Pat. No. 5,417,930 even suggests that a slurry-type reactor with internal circulation via one or more draft tubes can be particularly beneficial for the polymerization of polymerizable substances. For reactions including such substances the prior art also discloses a number of reactors for performing a heterogeneously catalysed reaction with external circulation of the slurry mixture. Thus for example U.S. Pat. No. 5,969,178 describes a process for continuous production of MMA from isobutylene or tert-butanol via methacrolein. An oxidative esterification of easily polymerizable methacrolein is carried out as the last step of the process in a bubble column with external circulation. The reactor is described as an "external circulation type bubble column reactor".

CN 101314120 describes a loop slurry reactor with external circulation of the slurry mixture for performance, for example, of the Fischer-Tropsch process. All reactors having external circulation of the slurry mixture require quite complex reactor designs and slurry conveying apparatuses that have to be safeguarded, for example, by means of further pumps. Therefore, and for other reasons, these systems thus have disadvantages compared to systems having internal circulation.

It may in principle be stated that suitable catalyst systems which are based on supported mixed metal oxide supports, contain nano-distributed gold in addition to other doping metals and doping elements and allow conversions and selectivities suitable for industrial use have been found. These catalyst systems are stirred in pulverulent form, i.e. the reaction is performed as a suspension or slurry catalysis.

Alternatively described are fixed bed systems in which the catalyst is fixed in the reactor as a pellet or shaped article. In order to allow long-term stable operation of these systems over years it is necessary to develop suitable reactors and reactor systems which ensure a minimum abrasion through mechanical and chemical influences.

In summary, the following aspects of the process according to the prior art are in need of improvement and desirable:
simplest possible construction of the reactor and thus unlimited suitability for scale-up
the use of substances that settle out or are readily polymerizabre is possible
use of high catalyst concentrations and hence higher throughput
reduced abrasion of the heterogeneous catalyst used
good commixing of the reactor phases
long catalyst on-stream time, robust operation without interruption, very short maintenance phases if any
the possibility of installation of simplified filtration systems for continuous separation of the heterogeneous catalyst from the slurry mixture without shutdown times The novel LiMA process for producing MMA combines the highly efficient process stages of C2-based methacrolein synthesis starting from ethylene and synthesis gas to afford methacrolein with the highly efficient direct oxidative esterification of methacrolein to afford MMA. Precisely this combination of established steps with novel developments has made it possible to provide a novel, highly efficient process for MMA production. In the first stage this process reacts ethylene with synthesis gas to afford propionaldehyde, wherein known rhodium-based phosphine or phosphite ligands are advantageously used as catalysts. In a modified process, reaction with formalin affords almost quantitative yields of methacrolein as an intermediate. In the last step, methacrolein is then converted directly into MMA in the presence of methanol over a noble metal-based heterogeneous catalyst, thus achieving high conversions and virtually quantitative selectivities.

In Angew. Chem. 2016, 128, 14420-14428, T 2016 Wiley-VCH Verlag GmbH & Co. KGaA, Weinheim, R. Cirminna and M. Pagliaro describe the essential aspects and features of a nanoparticulate gold-NiO$_x$-based catalyst of the Japanese MMA manufacturer Asahi Kasai Chemicals.

What appears to be essential to the performance of the active gold catalyst is inter alia the use of a mixed metal oxide support material which consists of aluminium oxide, silicon oxide and magnesium oxide and allows preparation of the complex gold-NiO$_x$ system. K. Suzuki, H. Ishida et al. describe the production of catalysts AuNiO$_x$/SiO2-Al2O3-MgO and a reaction system in ACS Catal. 2013, 3, 1845-1849, wherein the reaction of methacrolein in an oxidative esterification with methanol and an oxygen-containing gas, such as air in the simplest case, is performed continuously in a laboratory apparatus. These studies are material to catalyst selectivity for the reaction but give no indication of how a large industrial scale reactor may be configured to efficiently retain the catalyst and thus maintain performance in long-term operation.

A reactor for performing the oxidative esterification of methacrolein to MMA for example is described in EP 3 235 560. This document describes circulation of the triphasic medium through a so-called draft tube, i.e. a zone in which medium is conveyed downwards by means of a stirrer, while the gasified reaction space has the opposite flow. This is done to produce catalyst concentration gradients. There is a high catalyst concentration in the lower portion of the reactor and a lower catalyst concentration in the upper portion. Separation systems for achieving continuous more or less catalyst-free removal of product medium from the reactor are also proposed. This is accomplished with filters which are particularly preferably to have a retention of 10 to 50 μm. An additional preseparation of the catalyst by an assembly of inclined elements, so-called inclined settlers, is described.

Fines in the catalyst/fines that may be formed by abrasion during the reaction cannot be effectively retained/recovered according to this method. Another problem with this system is that gas separation before the filtration system is not described. However, both in the operation of the filter and in the inclined settling, gas fractions result in partial or complete failure of the separation effect/also lead to polymeric deposits of monomers in the reaction matrix.

Since the reactor is preferably to be used for a continuous process, the heterogeneous catalyst should be able to be continuously filtered out of the reaction mixture. To this end it is preferable to use filters present in the reactor, particularly preferably at the periphery of a zone 2 in the upper portion of the reactor. In particular, irrespective of the other embodiments of the invention chosen, preference is given to installing at least one continuously operable and backwashable filter in the upper portion of this zone 2.

Alternatively or in addition the reaction mixture is continuously discharged from the reactor and worked up/subjected to further treatment. This further treatment may be for example washing, reactivation or separation by particle sizes.

Furthermore, according to EP 3 235 560 an additional settling system may also be installed upstream of such filters or else at the periphery of the reactor. This may be a specific zone with laminar flow, where a majority of the catalyst used is sedimented. Such sedimentation is thus effected before the actual filtration. One possible variant of such a sedimentation system is, for example, an assembly composed of inclined elements, for example tubes or inclined metal sheets. The principle of operation of such systems is further described in Journal of Fluid Mechanics/Volume 92/Issue 03/June 1979, pp 435-457 and "Enhanced sedimentation in vessels having inclined walls" in Theory of Dispersed Multiphase Flow: Proceedings of an Advanced Seminar Conducted by the Mathematics Research Center The University of Wisconsin-Madison May 26-28, 1982. Details of use for an oxidation reaction, for example, are given in JP 10-094705 A and JP 09-248403 A.

JP 09-248403 A moreover describes an apparatus for workup of a triphasic reaction mixture (liquid-solid-gas) as may be employed for oxidative direct esterification of methacrolein to afford MMA. The chosen design of the inclined settler in conjunction with a degassing zone and a downcomer results in pressure differences over the vertically arranged inclined tube elements, the downcomer/inclined settler zone is degassed and thus largely depleted in oxygen, thus resulting in rather reductive conditions prevailing here. One problem observed is that of short circuit flows inside the inclined settler elements. This results in increased byproduct formation of isobutyraldehyde and methyl isobutyrate, i.e. in undesired hydrogenation products of methacrolein and MMA itself. In this publication these problems are solved by the incorporation of throttling elements into the inclined settler, i.e. internals which retard, hold up and thus uniformize the flow in the inclined settler elements. The problem of fine discharge of catalyst constituents and fines fractions which occur as a result of abrasion during long-term performance of the reaction is not described here and remains open.

JP 10-094705 A further describes a similar separation system for solid-liquid-gas reaction matrices with reference to the example of methacrolein conversion to afford MMA now with the additional feature of integration of the separation apparatus into a reactor tank (CSTR system). An essential feature is a sidewall in the reactor which fulfils the function of the downcomer. The inclined settler elements may be arranged inside and outside the reactor shell and this document too describes throttles, diaphragms inside the inclined settler elements which uniformize the flow and thus reduce the problem of byproduct formation.

Characterizing features for both Japanese applications are the parameters of operation of the downcomer and the inclined settler. While in the downcomer portion a very high velocity of the degassed slurry is established (0.5 to 1.5 m/sec) the discharge velocity at the outlet of the inclined tube elements is 0.004 m/sec (0.4 cm/sec or correspondingly 14.4 m/h). This high velocity difference of the downcomer velocity relative to the discharge velocity (0.5/0.004=factor of 125) is a consequence of the chosen design. Especially the high downwards velocity in the downcomer portion can lead to entrainment of small gas bubbles, thus impairing effective separation in the inclined settler or preventing its functioning. The corresponding Japanese patents do not address this problem and demonstrate the mode of operation using model systems of water and support material, pressurelessly too, which is unsuitable for describing the effective reaction solution of the direct oxidative esterification of methacrolein to afford MMA in the presence of a noble metal-containing oxidation catalyst.

These optimized catalysts too, and the reactor and separation systems described in the prior art, still have decisive disadvantages which lead to technical problems in continuous operation. On the one hand production, transport and reactor charging result in abrasion particles of particularly small diameter. On the other hand these particles are also formed over time in the reactor in continuous operation. These fine particles lead to a wide variety of problems:
  they have different activities and selectivities,
  their surface can host undesired side reactions, such as hydrogenation reactions in particular of C—C double bonds conjugated with the carbonyl unit. This occurs especially with Pt- or Pd-based catalysts when only very low oxygen concentrations are present locally, which can in turn occur as a result of an elevated activity of such catalyst fractions.
  they may be the subject of uncontrolled co-discharge which in continuous operation results in an economically disadvantageous loss of noble metal.
  the discharge can lead to problems in process management, in particular in conduits, columns or filters.

In summary, the following aspects of the prior art processes, especially in combination with one another, are in need of improvement:
  highest possible yield coupled with lowest possible proportion of byproduct, in particular saturated compounds such as methyl isobutyrate.
  targeted discharging only of the fine catalyst particles and thus only low noble metal losses.
  unproblematic process management in the workup and lowest possible maintenance cost and complexity thereof

SUMMARY OF THE INVENTION

Problem

The problem addressed by the present invention in view of the prior art is therefore that of providing a technically improved process for oxidative esterification of methacrolein that is not afflicted with the disadvantages of conventional processes.

A particular problem addressed by the present invention was that of providing an improvement in the workup of the crude product from an oxidative esterification of methacrolein and methanol to afford MMA and thus to improve the overall yield of such a process compared to the prior art.

A further problem addressed was that of removing from the reactor the greatest possible proportion of fine particles of the employed catalysts for the oxidative esterification within the shortest possible time after commencement of the continuous reaction.

A further problem addressed by the present invention was that of also removing fines fractions of the catalyst formed in continuous operation of the reaction and reducing and largely preventing the formation of fine particles by abrasion.

A further problem addressed was that of keeping the loss of noble metals employed in the catalyst as low as possible over the running time of the reaction.

A further particular problem addressed was that of providing a process where as few byproducts as possible, especially as little methyl isobutyrate, isobutyric acid and methyl propionate as possible, are formed.

Solution

The problems are solved by a process for producing alkyl methacrylates which is carried out in a reactor in the liquid phase starting from methacrolein by reaction thereof with an alkyl alcohol in the presence of an oxygen-containing gas and a particulate, pulverulent catalyst. It is preferable when the alkyl alcohol is methanol and the alkyl methacrylate is MMA.

This process features a reactor comprising at least the zones A, B and C. Zone A altogether comprises the zones A-1, A-2 and A-3. Zone B thus altogether comprises the zones B-1, B-2 and B-3—and Zone C the zones C-1, C-2 and C-3.

Zone A represents the primary reaction zone provided with at least one stirring means, wherein the stirring means ensures intensive commixing of the gaseous, liquid and solid phases in this zone A. The stirring means ensures that turbulent flows are generally present in this zone A. On average an upwards flow is present in zone A.

The invention also includes the following embodiments:
  1. Process for producing alkyl methacrylates starting from methacrolein by reaction thereof with an alkyl alcohol in the presence of an oxygen-containing gas and a particulate, pulverulent catalyst in the liquid phase in a reactor, characterized in that this reactor comprises at least the zones A, B-1, B-2, B-3 and C, wherein more than one of the respective zones B-1, B-2 and C may in each case be present and wherein
    (i) zone A represents the primary reaction zone and is provided with at least one stirring means, wherein the stirring means ensures intensive commixing of the gaseous, liquid and solid phases in zone A, (ii) zone B-1 is provided with internals for flow calming which very largely prevent entry of the gaseous phase into the subsequent zones B-2, B-3 and C,
(iii) zone B-3/zones B-3 contains a reaction mixture which has been very largely freed of gaseous phase and is connected to zone C and
(iv) zone C/zones C comprises a continuously classifying sedimentation apparatus, wherein the average vertical flow in zone A and C is upwards and in zones B-1, B-2 and B-3 is downwards and
(v) the energy input for suspension of the heterogeneous pulverulent oxidation catalyst by means of the stirrer and the stirring means is limited to not more than 3 kilowatts per cubic meter of reaction mixture.

2. Process according to embodiment 1, characterized in that
a portion of the reaction mixture from zone B-2 enters zone C and the particulate, pulverulent catalyst is in the sedimentation apparatus separated into two fractions in such a way that a fraction of relatively small catalyst particles, at least 60% by weight of which have a size of less than 20 μm, and a fraction of the remaining, on average relatively large, catalyst particles are obtained,
in that the relatively small catalyst particles exit the reactor with the reaction mixture at the outlet of zone C and in that the concentration of the discharged particles in the reaction matrix is between 1 and 200 ppmw.

3. Process according to embodiments 1 and 2, characterized in that the energy input for suspension of the heterogeneous pulverulent oxidation catalyst and for the purpose of gas dispersion by means of the stirrer and the stirring means is limited to 0.05 to 1.0 kW per cubic meter of reaction mixture.

4. Process according to embodiments 1 or 2, characterized in that the reactor comprises a triphasic zone A-2 or A-3 which is arranged above the zone A-1 and does not have a stirrer, wherein no further gas bubble dispersion is brought about by the effect of the stirrer.

5. Process according to at least one of embodiments 1 to 3, characterized in that the alkyl alcohol is methanol and the alkyl methacrylate is MMA.

6. Process according to at least one of embodiments 1 to 4, characterized in that the reaction is performed in a reactor having a ratio of diameter to height of the gasified fluid level between 1:1 and 1:50.

7. Process according to at least one of embodiments 1 to 6, characterized in that at the transition of zone A to every zone B internals are present which effect flow uniformization of the reaction mixture upon entry of the reaction mixture into zone B.

8. Process according to at least one of embodiments 1 to 7, characterized in that the ratio of the volume of zone A to the total volume of all zones B and C is greater than 1 and less than 500.

9. Process according to at least one of embodiments 1 to 8, characterized in that the reactor generally has one or more feed conduits through which mixtures of alkyl alcohol, MMA, methacrolein, water and optionally alkali metal salts of methacrylic acid dissolved in this mixture may be added and these feed conduits may optionally be distributed over the vertical height of the reactor.

10. Process according to at least one of embodiments 1 to 9, characterized in that the sedimentation apparatus consists of a plurality of channel-like profiles, tubes or lamellae having an angle of inclination to the horizontal.

11. Process according to embodiment 9, characterized in that the channel-like profiles, tubes or lamellae have the same pressure at the inlet.

12. Process according to at least one of embodiments 1 to 10, characterized in that the sedimentation apparatus is an inclined settler or a hydrocyclone.

13. Process according to at least one of embodiments 1 to 12, characterized in that the relatively large catalyst particles are retained in the sedimentation apparatus C and recycled into zone B-3 and in that the relatively small catalyst particles are collected using a filter system.

14. Process according to at least one of embodiments 1 to 13, characterized in that zone A in the lower portion of the reactor is preferably actively supplied with an oxygen-containing gas via corresponding nozzles or gasification apparatuses and the at least one zone B preferably does not comprise any apparatuses for active gasification of the reaction mixture.

15. Process according to at least one of embodiments 1 to 14, characterized in that zone A, in particular zones A-2 and A-3, and the at least one zone B, in particular zones B-2 and/or B-3, are separated from one another by dividing walls.

16. Process according to at least one of embodiments 1 to 15, characterized in that the internals at the transition of zone A, in particular of zones A-2 and A-3, to every zone B largely prevent entry of gas bubbles into zone B.

17. Process according to at least one of embodiments 1 to 16, characterized in that the average catalyst particle size of the employed catalyst is between 20 and 120 μm.

18. Process according to at least one of embodiments 12 to 17, characterized in that the filter system comprises at least two successively traversed filters downstream of the elements of zone C, wherein the first filter collects coarse particles having a diameter greater than 5 μm and the second filter collects fine particles having a diameter greater than 0.1 μm.

DETAILED DESCRIPTION OF THE INVENTION

Figure 1:
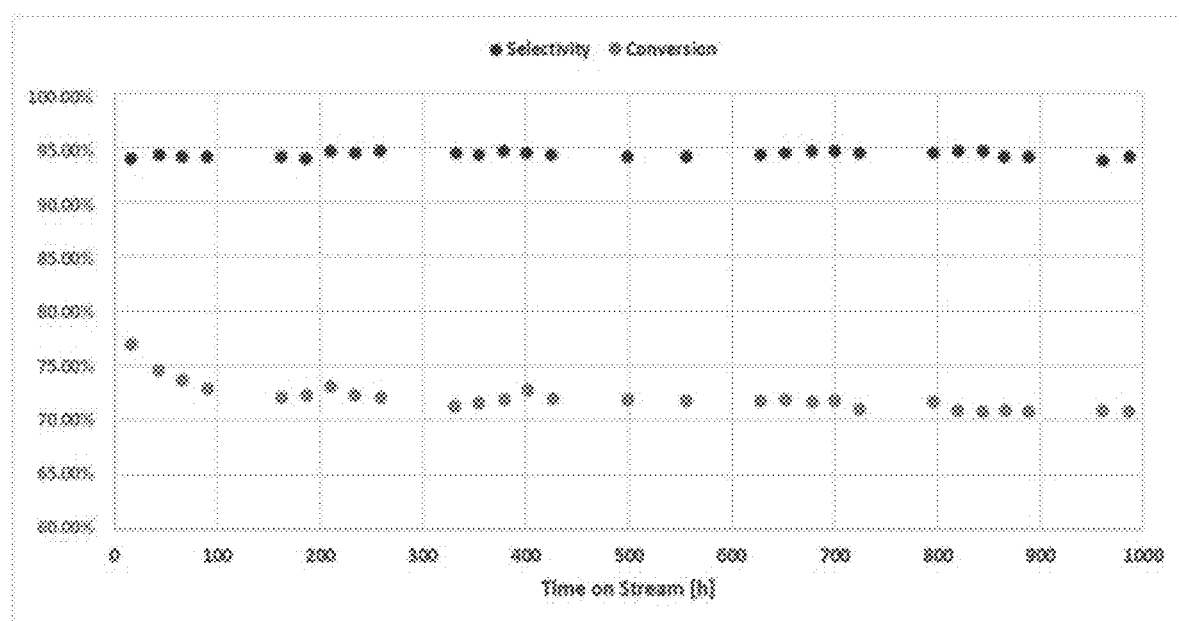
FIG. 1 shows progress of conversion and selectivity over 1000 operating hours in continuous operation according to examples.

Zone A is generally characterized by the presence of three phases that differ in terms of their physical state:
- the liquid phase consists of the organic matrix and contains gas constituents such as nitrogen and oxygen dissolved under the prevailing reactor pressure
- a further phase is a gas phase which consists substantially of oxygen and nitrogen—this gas phase is in the form of gas bubbles having different bubble diameters which may change over the height of zone A
- a solid phase which consists of a solid catalyst powder insoluble under the reaction conditions. The catalyst is suspended in the reaction matrix by the stirrer elements.

Above the reaction zone A is a gas phase or a gas space which is arranged inside the reactor shell. The gas space consists of the reaction gas composition and has an oxygen content substantially lower than the freshly introduced oxidation gas used. In the simplest case air is used and supplied to the reactor by means of one or more separate conduits via a compressor. The compressed gas mixture may optionally be dewatered and preheated before introduction into the reactor, with possible advantages for reaction management with regard to the secondary component spectrum and continuous operability of the reactor. An excessively cold oxidation gas can for instance result in precipitation of salts and thus blockage of the feed point. An excessively moist oxidation gas increases the water content in the reaction matrix, thus potentially resulting in increased formation of water addition products.

The zones A-1, A-2 and A-3 which are preferably to be distinguished and together form zone A, have the following features:

Zone A-1 is a triphasic domain in which the three phases, solid in the form of the catalyst particles, gas phase, for example air as the oxidation medium, and liquid as the reaction matrix, are present. The reaction zone of zone A-1 is thus present with approximately homogeneous distribution of catalyst particles and virtually constant slurry density, with gas introduction for example via spargers.

Zone A-2 which is generally arranged thereabove is likewise a triphasic domain comprising three analogous phases where, due to a reduced effect of the stirrer, a lower suspension density of solids particles compared to zone A-1 is present. The oxygen concentration is generally likewise reduced compared to zone A-1.

In a preferred embodiment the reactor additionally comprises at least one, preferably precisely one zone A-3. This zone A-3 is arranged above zone A and does not itself comprise a stirrer. Compared to zone A there are fewer turbulent flows present here and a portion of the solid phase can sediment out of the triphasic liquid/solid/gaseous reaction mixture. The reaction mixture flows from zone A-3 into zone B. The transition zone A-3 is likewise a triphasic domain comprising three analogous phases where due to a further reduced effect of the stirrer an even lower suspension density of solids particles compared to zones A-1 and A-2 is present.

In zones A-2 and in particular A-3 there is in general thus markedly reduced, preferably no further, gas bubble dispersion brought about by the effect of the stirrer.

The zones B-1, B-2 and B-3 which are to be distinguished and together form zone B, have the following features:

Zone B-1 may be in the form of one or preferably two or more separate zones B-1, wherein zones B-1 to B-3 are preferably arranged at the reactor edge.

Zone(s) B-1 are provided with internals for flow calming which very largely prevent entry of the gaseous phase into the subsequent zones B-2, B-3 and C. Zone B-1 is typically biphasic (solid-liquid), wherein a small proportion of gaseous bubbles may be present. The downward flow velocity in zone B-1 is less than the ascent velocity of the bubbles. Zone A and at least one zone B-1 are preferably separated from one another by internals or other apparatuses such that the reaction mixture from zone A flows into zone B optionally via zone A-2 and/or A-3. This entry is particularly preferably effected in the uppermost third of zone B.

Zone B-2/zones B-2 contains a reaction mixture which has been very largely freed of gaseous phase. Zone 8-2 serves as the feed zone for zone B-3 and zone C. This zone B-3 which has likewise been very largely freed of gaseous phase generally has a flow velocity elevated compared to zone B-2 but need not host a turbulent flow. The flow velocity in zone B-3 should also be greater than the flow velocity in zone A-1 and A-2 since otherwise the internal loop in the reactor could collapse and gas would enter zone B-3 from below from zone A-1 and the sedimentation apparatus would thus be disturbed.

Zones B-3 are the transition region to zones C, wherein zones B-3 are generally arranged very largely below zones B-2 and C.

Zone B-3 also has an opening to zone A, thus allowing a portion of the reaction mixture freed of fine catalyst particles to flow back into zone A via this opening.

According to the invention the average vertical flow is oriented upwards in zone A-1 to A-3 and downwards in zones B.

A zone C-1 which may also be referred to as a rest zone, as part of zone C, additionally promotes the subsequent settling of the relatively large catalyst particles in the sedimentation apparatus.

Generally every zone B-2 is in each case connected to at least one zone C directly and/or indirectly via zone B-3, wherein zone C comprises a continuously classifying sedimentation apparatus and thus constitutes the actual region for sedimentation. A portion of the reaction mixture from zone B-3 enters zone C and the particulate, pulverulent catalyst is in the sedimentation apparatus preferably separated into two fractions in such a way that a fraction of relatively small catalyst particles, at least 60% by weight of which, preferably at least 80% by weight of which, have a size of less than 20 μm, and a fraction of the remaining, on average relatively large, catalyst particles are obtained. The relatively small catalyst particles thus exit the reactor with the reaction mixture at the outlet of zone C, in particular of zone C-3. It is also preferable when the concentration of the discharged particles in the reaction matrix is between 1 and 200 ppmw.

The optional zones C-1, C-2 and C-3 which are to be distinguished and together form the zone C, have the following features:

Optional zone C-1 is the entrance to the lamella and inclined settler elements for uniformization and retardation of the flow and separation of the solids particles from the reaction liquid.

Optional zone C-2 comprises a perforated plate and/or flow resistance elements at the outlet of the individual inclined settler elements. Smaller perforated plate areas can result in polymer deposits and thus blockages in the apparatus after extended continuous operation. Larger areas of the perforated plates can in turn result in short circuit and recirculating streams in the apparatus.

Optional zone C-3 is a collection chamber for reaction solution which is low in particles or free from particles. The reaction solution is generally under pressure and contains physically dissolved gas constituents. Before being sent for workup, for example to a rectification or extraction, the solution may be decompressed and very largely degassed.

The employed catalyst particles generally have an average size between 50 and 120 µm, preferably between 50 and 100 µm, particularly preferably between 70 and 90 µm. According to the invention the volume-average catalyst particle size is measured according to ISO 13320-1 with an LS 13 320 particle size measuring apparatus from Beckman Coulter.

The pulverulent fresh catalyst employed for the oxidative conversion of methacrolein comprises active noble metal, such as gold, platinum or palladium, as the central active oxidation metal in a concentration of between 0.1% by weight and 10% by weight based on the total weight including further support material, for example. The particles of the catalyst have a size of for example between 0.1 and 300 µm, wherein more than 95% by volume of the catalyst particles present have a size of less than 200 µm. It is preferable for such a catalyst when more than 58% by volume of the catalyst particles have a size between 10 and 90 µm and the fines fraction of the catalyst particles in the reactor having a size of 0.1 µm to 10 µm is less than 10% by volume upon charging.

In the case of such a catalyst system for example less than 0.5% by weight per hour of the catalyst powder present in the reactor is discharged from the reactor in a classifying manner together with the product solution during the reaction. Thus after 1000 operating hours the catalyst fraction remaining in the reactor therefore preferably comprises more than 98% by volume of all catalyst particles having a size greater than 10 µm. Furthermore, the discharged catalyst is collected in at least one further filter which allows retention of particles of 1 to 30 µm and the particles retained in the filters downstream of the sedimentation apparatus are to an extent of more than 50% by volume particles smaller than 30 µm.

It is preferable when the ratio between the average vertical, generally downwards, flow velocity in zone B and the average vertical, generally upwards, flow velocity in zone A is between 5 and 50, preferably between 10 and 40.

The reaction mixture in zone A may optionally be vertically conveyed using at least one pump. However, the stirrer is usually sufficient therefor.

Preferred reaction parameters are as follows:
a. the reaction in the reactor is carried out at a pressure in the range from 2 to 50 bar and at a pressure in the range from 10° C. to 200° C. at a molar ratio of methanol to methacrolein in the range from 1:1 bis 50:1,
b. in the reactor the molar ratio between the steady-state concentrations of the alkyl alcohol and of the methacrolein is less than 30 to 1,
c. the oxygen concentration in the gas phase in the individual reactors at the site of offgas removal is below the explosive limit of the issuing gas mixture or less than 7% by volume,
d. the steady-state ratio of alkyl alcohol to methacrolein in the reactor to the molar ratio of the substances in the feed in the steady state is between 1.5 and 10,
e. the steady-state concentration of methacrolein in the individual reactors is less than 21% by weight.

The reaction may optionally be performed in a plurality of reactors connected in parallel.

The sedimentation apparatus of zone C per se preferably consists of a plurality of channel-like profiles, tubes or lamellae. These preferably have an angle of inclination to the horizontal. The sedimentation apparatus is particularly preferably an inclined settler.

Zone B-1 preferably comprises (honeycomb) tubes, cuboids or discs at the entrance to realize a uniform flow. It is similarly preferable when the entrances to all channel-like profiles, tubes or lamellae are at the same height at the transition of zone B-3 to C-1. These measures make it possible to achieve uniform pressure conditions at the entrance to the sedimentation apparatus. It is thus particularly preferable when most, in particular all, channel-like profiles, tubes or lamellae have the same pressure at the inlet.

Alternatively, the sedimentation apparatus used may be a hydrocyclone.

As a result of the sedimentation apparatus the relatively large catalyst particles are retained in this sedimentation apparatus C and recycled into zone B-3. The relatively small catalyst particles pass through the sedimentation apparatus and are separated from the reaction solution using a filter system outside the reactor and may be recycled.

Also particularly preferred is an embodiment in which the filter system comprises at least two successively traversed filters downstream of the elements of zone C. The first filter is suitable for separating coarse particles having a diameter greater than 20 µm, preferably greater than 5 µm. The second filter in turn serves to collect fine particles having a diameter greater than 0.1 µm. In such an embodiment it is then possible for example to recycle the particles collected in the first filter to the reactor by backwashing, for example with filtered reactor discharge. To this end there are ideally two filters connected in parallel, one of which has reactor discharge from the sedimentation apparatus flowing through it and the second of which is subjected to backwashing.

The solids of the second filter are by contrast removed and subjected to further processing for example through incineration of the filter for recovery of the catalyst, in particular the noble metal present therein. During this removal of the filter the reactor discharge containing the catalyst is ideally passed through a second identical filter connected in parallel.

In an exemplary embodiment of the process for elucidation of the invention the process is performed at an average sedimentation velocity of 10 m/h. In this case the superficial velocity is for example 7 m/h.

The reaction is preferably performed in a reactor having a ratio of diameter to height of the gasified fluid level between 1:1 and 1:50. It is likewise preferable when the ratio of the volume of zones A to the total volume of all zones B and C is greater than 1 and less than 500.

It is likewise preferable when at the transition of zone A, in particular of zone A-2, to every zone B internals are present which effect flow uniformization of the reaction mixture upon entry of the reaction mixture into zone B, in particular into zone B-1, This largely prevents gas bubbles passing from zone A into zone B, in particular into zone B-1. The internals are preferably elements made of plastics that are resistant to the reaction medium, for example PVC, PEEK or other polymeric materials. It is alternatively possible to employ metallic tubes, which may be square, rectangular or polygonal, plates or wire meshes which serve to reduce the Reynolds number of the suspension. While the Reynolds number in zone A/A-2 generally has values of 10 000 or more, as a consequence inter glia of turbulent flow in the reaction space, the Reynolds number in zone B-1 is markedly reduced by the apparatus geometry and the internals. In the internals it can be shown by CFD simulation that the downward flow is retarded to such an extent that the gas bubble ascent velocity is comparatively higher and at this point the suspension is depleted in gas or is physically gas-free. The gas bubble ascent velocity in the steady-state reaction medium is generally about 0.05 m to 0.5 m per second. The lower limit of velocity has a determining influence on the mode of operation and the configuration of the apparatus and the internals. This ensures that the triphasic mixture of gas, liquid and solid catalyst can be safely converted into a biphasic suspension. This means that the gas bubbles escape upwards and do not pass into the inclined settler (Zone C). The absence of gas bubbles preferably has a determining influence on ensuring the mode of operation of the inclined settler.

The reactor generally has one or more feed conduits through which mixtures of alkyl alcohol, MMA, methacrolein, water and optionally alkali or alkaline earth metal salts of methacrylic acid dissolved in this mixture may be added. Some or all of these components may be supplied through separate feed conduits. The MMA is in this case a constituent of an optional recycling stream which is separated off at a subsequent point of the workup. Introduction is optionally and preferably carried out distributed over the vertical height of the reactor.

Zone A in the lower portion of the reactor is preferably actively supplied with an oxygen-containing gas via corresponding nozzles or gasification apparatuses. By contrast, the at least one zone B preferably does not comprise any apparatuses for active gasification of the reaction mixture.

The process according to the invention can be best performed when a stirring means is arranged in zone A. The stirring means is preferably a stirrer having at least 3 to 4 stages of blades which are for example arranged one above another and skewed relative to one another.

According to the invention, the process is moreover performed such that the energy input for suspension of the heterogeneous pulverulent oxidation catalyst by means of the stirrer and the stirring means is limited to not more than 3 kilowatts per cubic meter of reaction mixture. It is especially preferable when the energy input for suspension of the heterogeneous pulverulent oxidation catalyst and for the purpose of gas dispersion by means of the stirrer and the stirring means is limited to 0.05 to 1.0 kW per cubic meter of reaction mixture.

It is also preferable when zone A, in particular zones A-2 and A-3, and the at least one zone B, in particular zones B-1 and B-2, are separated from one another by dividing walls. It is particularly preferable when the internals at the transition of zone A, i.e. A-2 to A-3, to every zone B largely prevent entry of gas bubbles into zone B.

The selection and design of the stirrer especially has an effect on a. controlling the kinetics of the reaction and generally the reactivity of the system, b. ensuring hydraulic and mechanical functions of the reaction and the reactor, c. ensuring suspension of the catalyst in the reaction zone A, d. minimizing mechanical stress and thus abrasion of the catalyst and e. ensuring the gas dispersion and the distribution of the gas supply in zone A.

A number of requirements of the stirrer and the operation thereof in combination with the reaction kinetics initially appear contradictory per se: For an ideal mixture and rapid mixing of all reactants and auxiliaries, for example the basic solution incorporated to control the pH, and for efficient removal of the heat of reaction and also to prevent pH gradients within the reactor, high stirrer speeds and relatively large stirrer diameters are an obvious solution. On the other hand an excessively high speed and an excessively large diameter of the stirrer as well as certain stirrer blade geometries result in high local shearing of the reaction mixture and in mechanical abrasion of the catalyst.

The process according to the invention is preferably optimally performed such that the stirrer geometry and the number and geometry of the stirrer elements and the operating conditions are precisely adapted to the physical properties of the catalyst and the requirements of the reaction system. In this regard it was found that the energy input of the stirrer P (for power) is an essential criterion for controlling and very largely preventing abrasion of the catalyst. A criterion derived therefrom is the specific energy input which relates to the volume of the reaction matrix under real steady-state conditions, this being defined as P/V with units of kW per cubic meter [kW/m3].

It is here ensured for the direct oxidative oxidation of MAL to afford MMA in the presence of a suspended pulverulent noble metal-containing catalyst that the liquid is well commixed or homogenized or in the present triphasic system that the catalyst is sufficiently suspended in zone A. Further objectives for the present reaction system include improving mass transfer, heat transfer or the dispersion state of the oxidation gas.

All of these functions depend on the substance properties of the reaction matrix—for example viscosity and density—and the construction of the stirring apparatus. Taking into account the specific reaction matrices of the continuous reaction system for direct oxidative esterification of methacrolein to afford MMA it shall now be demonstrated which aspects of mixing science must be considered to ensure a multi-year service life and lifetime of the catalyst.

These correlations are described in the standard texts in fluid dynamics and mixing technology, and an example of this prior art for calculating power input and specific power input that may be mentioned here is Klaus Himmler, Wilfried F. Schlerholz, Chemie Ingenleurtechnik 2004, 76, 3, pages 212-219. This document specifies the important correlations of a general nature between stirrer constants (Newton number), Reynolds number, stirrer diameter and stirrer speed as well as formulae for calculation and configuration of stirrers. Information on the requirements and specific demands and problems in MAL conversion into MMA by means of the DOE reaction are not provided in this literature.

It has been found that the power input is usually an essential aspect for meeting the requirements of a high space-time yield coupled with a long lifetime of the catalyst. The power input P describes how much of the employed mechanical power arrives in the reaction medium and how much mechanical energy the catalyst is exposed to. The power input P is determined by the stirrer (type and size) and the stirrer speed. The following generally applies:

$$P = Ne * p * N^3 * d^5$$

Power input $P$=Newton number*density*stirrer speed$^3$*stirrer diameters

It is apparent from the formula for determining power input which influences must particularly be taken into account here. The dimensionless parameter, the so-called Newton number (Ne), is a function of the type of stirrer and varies from stirrer to stirrer. The Newton number is further determined by the substance properties of the reaction system. In the case of the DOE of MAL to afford MMA this is a reaction matrix containing methanol, methacrolein, MMA, water and a wide variety of organic compounds and salts as well as gas and solid. In particular, the density of the reaction matrix to be stirred is likewise important, in the case of DOE the density at reaction temperature is between 0.8 and 0.9 g/ml.

However, further potentially important influencing parameters for solving the problem addressed by the invention include the stirrer speed which is a third power variable for power input and the diameter of the stirring means which is a fifth power variable for power input.

The process according to the invention can be best performed when one or more stirring means are arranged in zone A, wherein the specific power input resulting from the four factors (see above) has a value between 0.01 and 3 kilowatts per m$^3$ of the reaction suspension. A power input between 0.05 and 1 kilowatt per m$^3$ of reaction matrix is particularly preferred. A specific power input between 0.05 and 0.5 kilowatts per m$^3$ of reaction matrix is very particularly preferred.

The type of stirring means has a determining influence on the Newton number (dimensionless number). The employed stirring means is generally selected such that the Newton number in the specific stirrer system is in the range from 0.1 to 10. Stirrers having a specific Newton number of 0.5 to 5 are particularly preferred. Stirrers having a specific Newton number of 0.5 to 1.5 are very particularly preferred. Depending on the size of the reactor it may be preferable to mount different stirrer types on one shaft, wherein the stirrers then have the same stirrer speed but may well have different Newton numbers and different diameters of the stirrer blades.

The stirring means is preferably a stirrer having at least 3 to 4 stages of blades which are arranged one above another and skewed relative to one another, for example.

It is also preferable when zone A, in particular zones A-2 and A-3, and the at least one zone B, in particular zones B-2 and/or B-3, are separated from one another by dividing walls. It is particularly preferable when the internals at the transition of zone A, in particular zones A-2 and A-3, to every zone B largely prevent entry of gas bubbles into zone B.

LIST OF REFERENCE SYMBOLS

FIG. 1: Progress of conversion and selectivity over 1000 operating hours in continuous operation according to examples.

Figure 2:
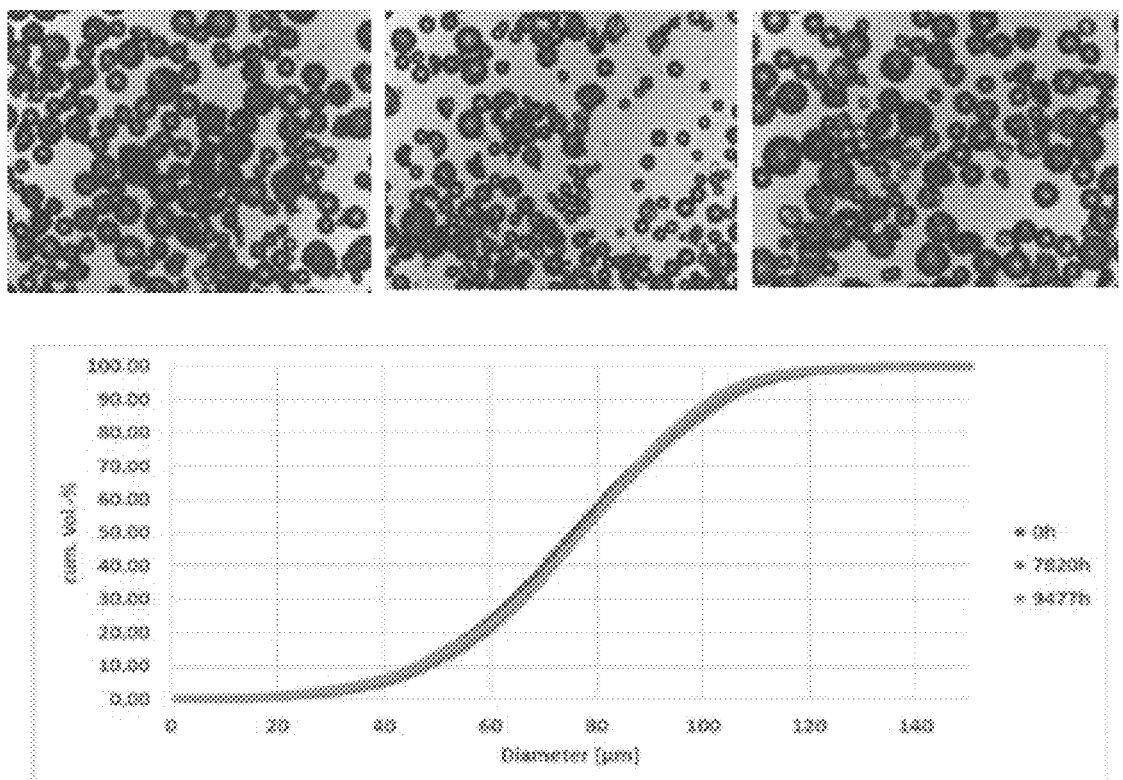
FIG. 2 shows micrographs of catalyst samples and particle size analyses at various operating junctures where "0 h" represents fresh catalyst.

FIG. 2: Micrographs of catalyst samples and particle size analyses at various operating junctures where "0 h" represents fresh catalyst.

Figure 3:
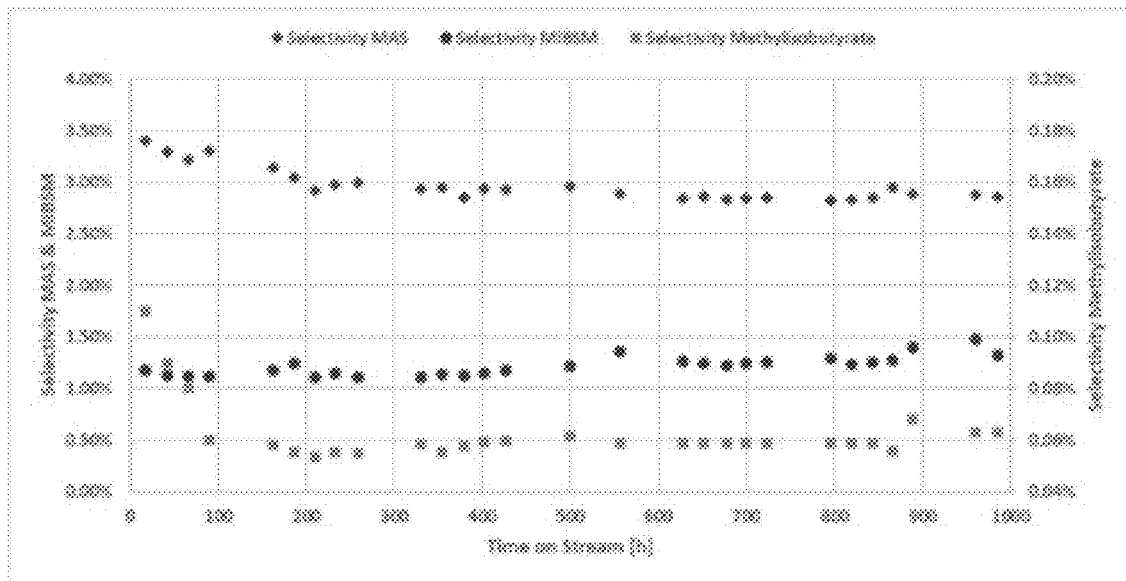
FIG. 3 shows evolution of selectivities for specific byproducts over 1000 operating hours in continuous operation according to examples.

FIG. 3: Evolution of selectivities for specific byproducts over 1000 operating hours in continuous operation according to examples.

Figure 4:
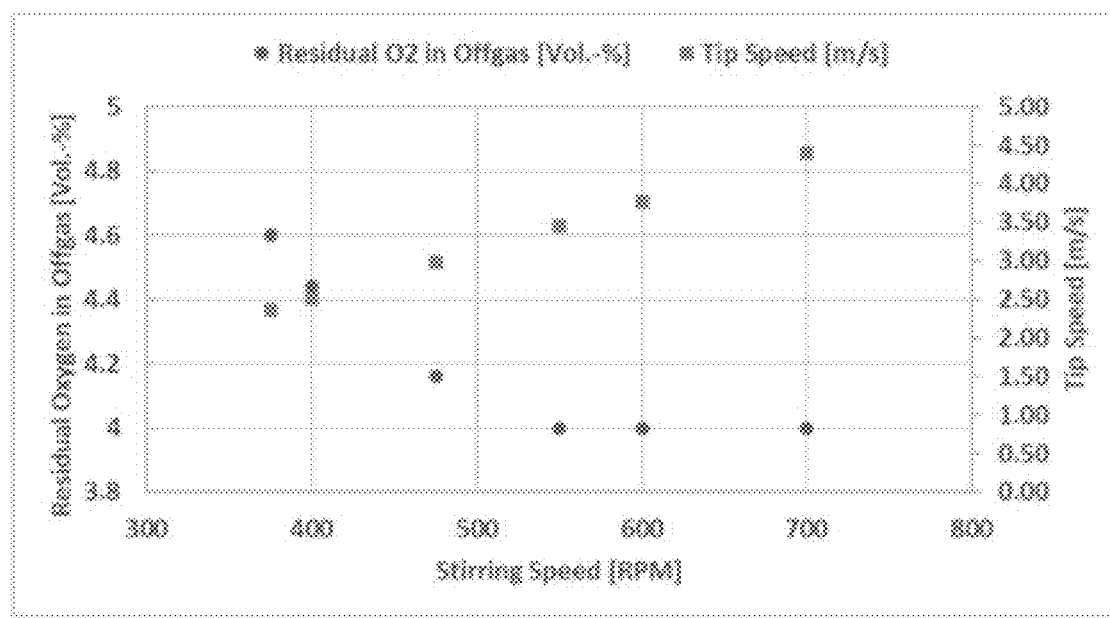
FIG. 4 shows correlations between stirrer speed/orbital velocity of the stirrer and resulting residual oxygen content in the emission gas.

FIG. 4: Correlations between stirrer speed/orbital velocity of the stirrer and resulting residual oxygen content in the emission gas.

Figure 5A:
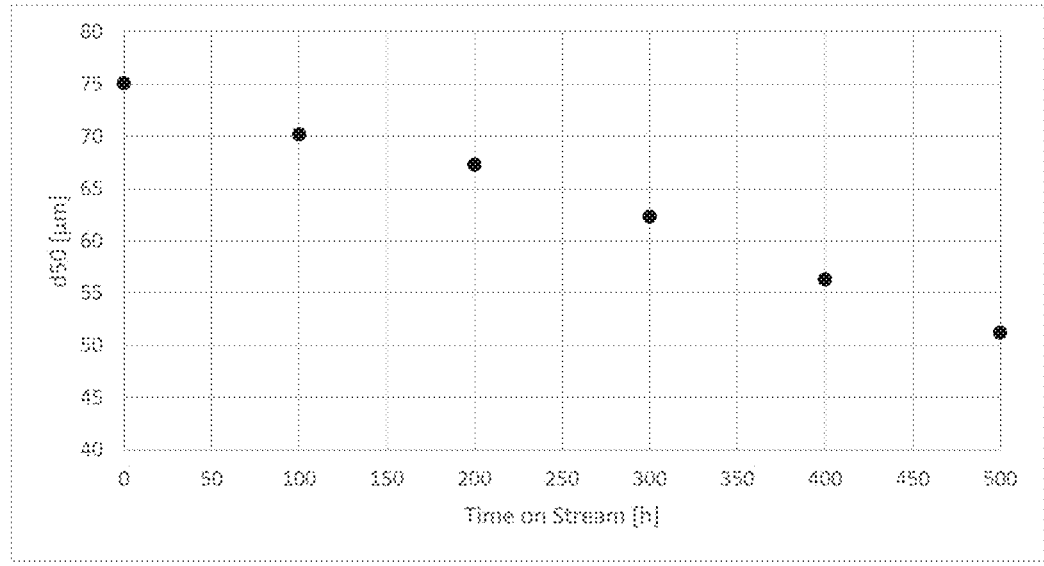
FIG. 5A shows an evolution of average catalyst particle diameter from comparative test 4g.

FIG. 5A: Evolution of average catalyst particle diameter from comparative test 4g: Determination of average particle diameter after respective 100 h intervals at a total experimental duration of 500 h and a specific power input of more than 3 kW per cubic meter.

Figure 5B:
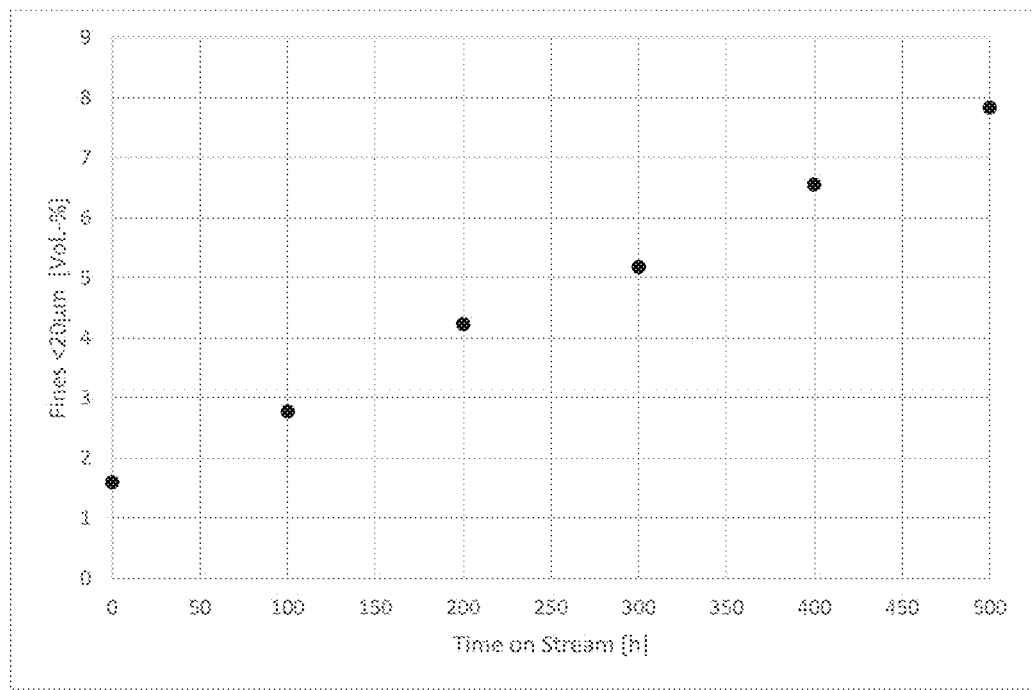
FIG. 5B shows a determination of particle fines fraction from comparative test 4g.

FIG. 5B: Determination of particle fines fraction from comparative test 4g: Determination of volume fraction in percent of all particles having an average diameter of less than 20 μm after respective 100 h intervals at a total experimental duration of 500 h and a specific power input of more than 3 kW per cubic meter.

Figure 6:
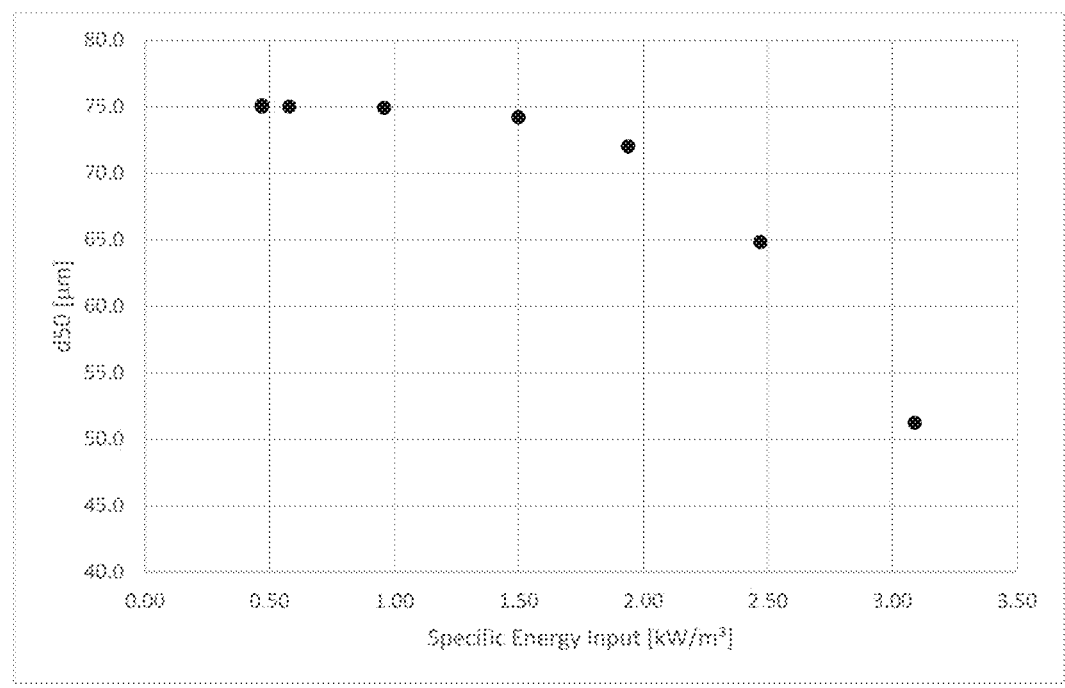
FIG. 6 shows results of experimental series 5a to 5 f.

FIG. 6: Results of experimental series 5a bis 5 f: The d50 of the particles after respective 500 h operating time intervals is plotted. Above a power input of more than 2 kW per cubic meter the d50 falls markedly with longer operating time, thus indicating excessively high catalyst abrasion.

Figure 7A:
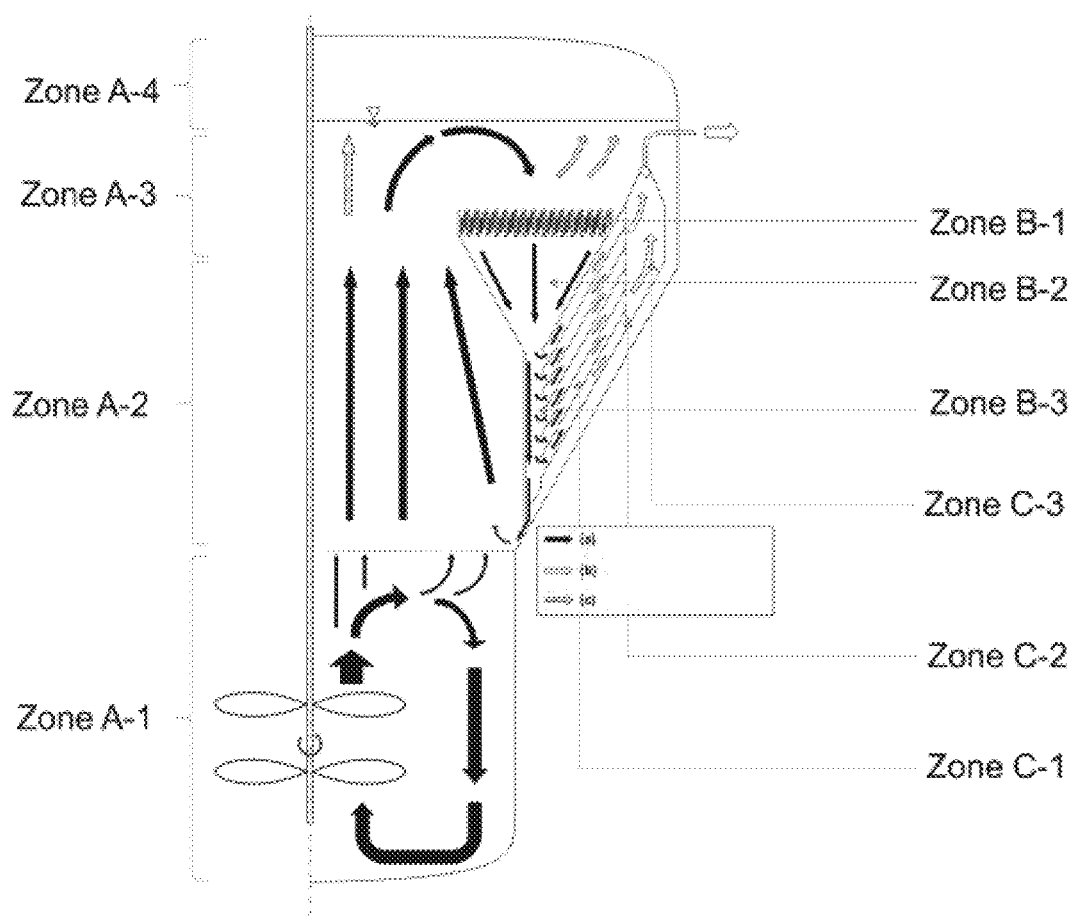
FIG. 7A shows an exemplary, axisymmetric embodiment of an exemplary DOE reactor having a stirrer and a wide variety of separating zones and inclined lamella settler packs with a vertical arrangement of lamellae.
Figure 7B:
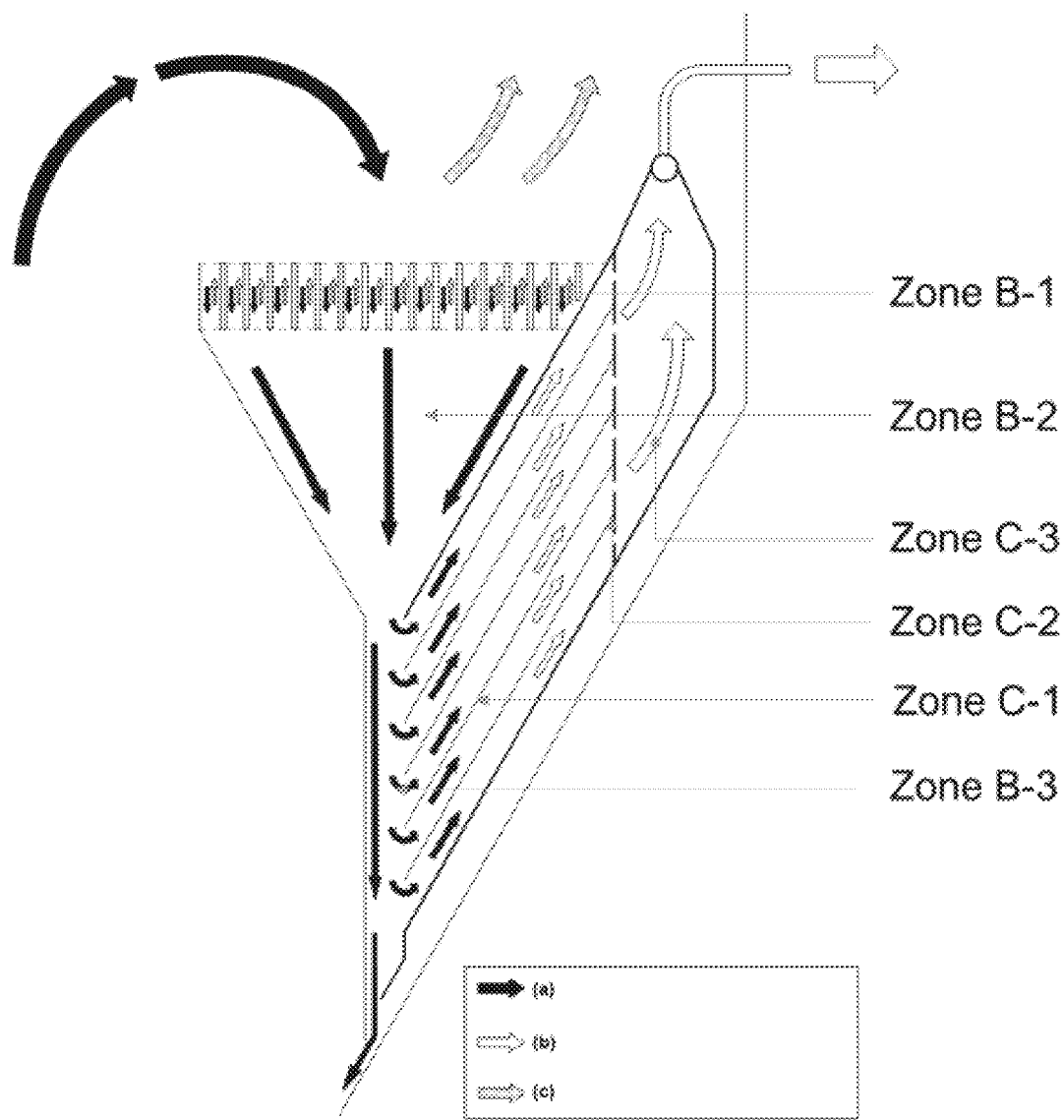
FIG. 7B shows an enlarged view of the inclined settler system and its inlet region from FIG. 7A.
Figure 7C:
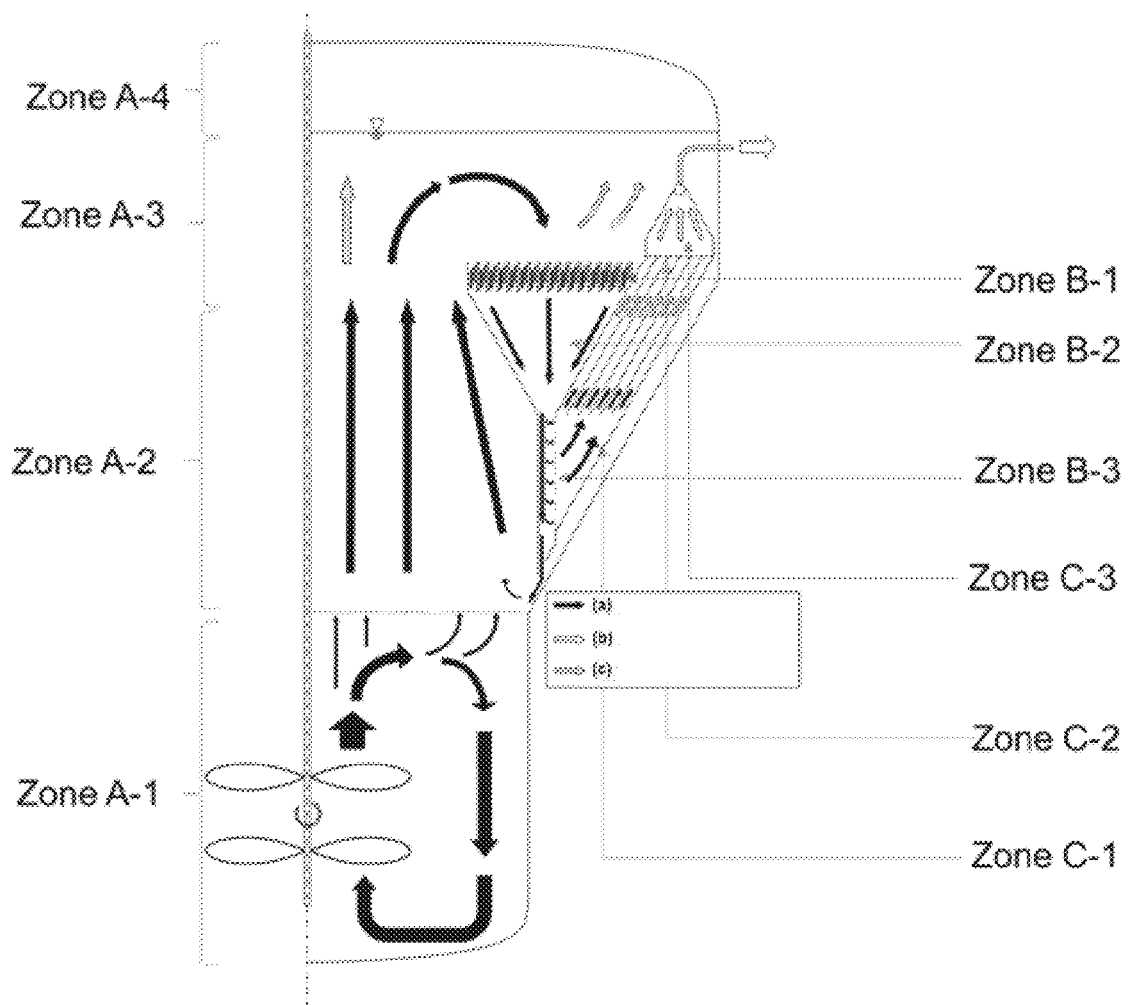
FIG. 7C shows a further exemplary, axisymmetric embodiment of an exemplary DOE reactor having a stirrer and a wide variety of separating zones and inclined lamella settler packs with a horizontal arrangement of lamellae.
Figure 7D:
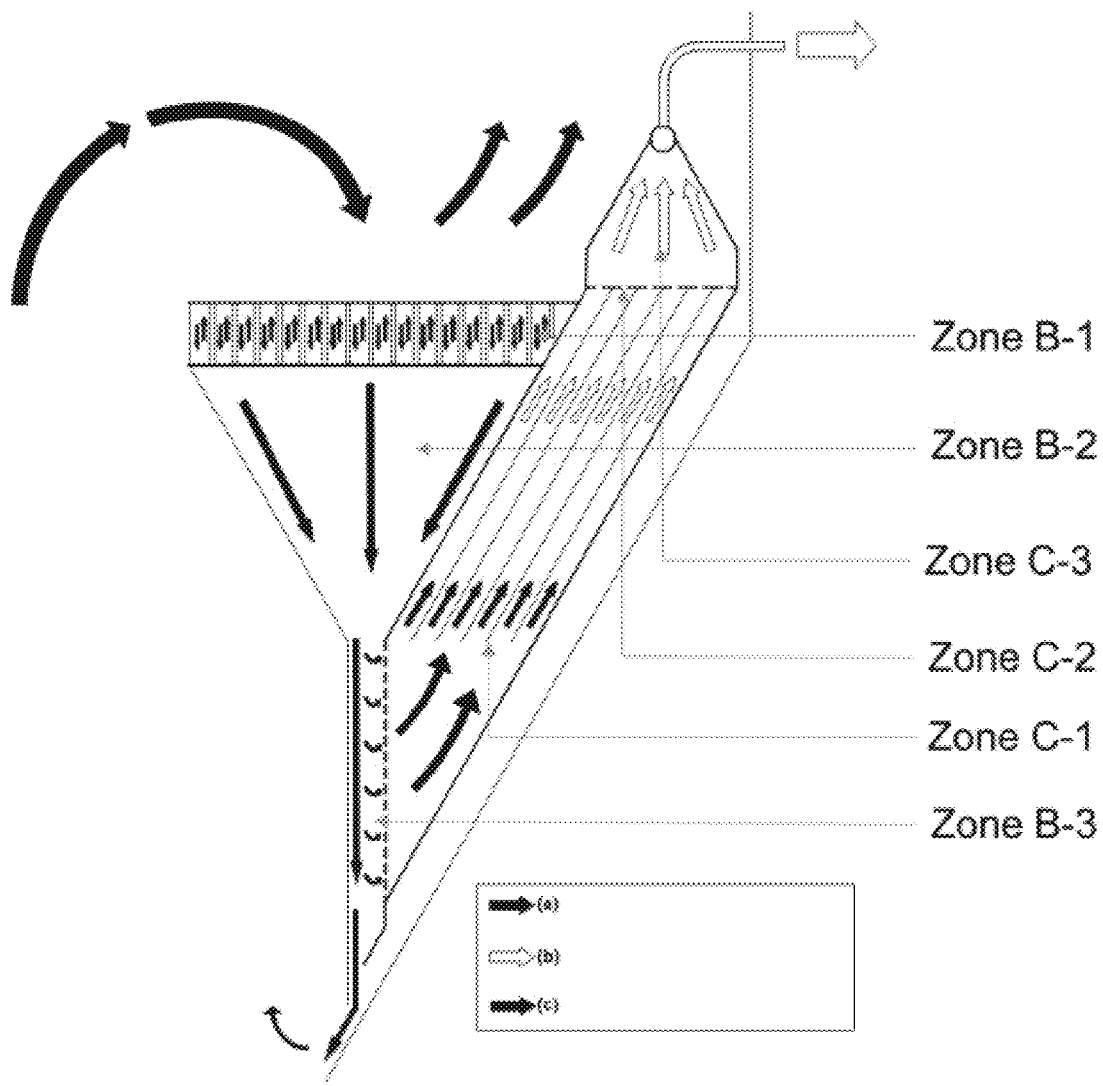
FIG. 7D shows an enlarged view of the inclined settler system and its inlet region from FIG. 7C.

FIG. 7A: Exemplary, axisymmetric embodiments of an exemplary DOE reactor having a stirrer and a wide variety of separating zones and inclined lamella settler packs with a vertical arrangement of lamellae FIG. 7B: Enlarged view of the inclined settler system and its inlet region from FIG. 7A FIG. 7C: Exemplary, axisymmrnetric embodiments of an exemplary DOE reactor having a stirrer and a wide variety of separating zones and inclined lamella settler packs with a horizontal arrangement of lamellae FIG. 7D: Enlarged view of the inclined settler system and its inlet region from FIG. 7C Details for FIGS. 7A, 7B and 7C:

Zone A-1: 3-phasic domain: Presence of solid (catalyst particles), gas phase (for example air as oxidation medium), liquid; reaction zone with approximately homogeneous distribution of catalyst particles and virtually constant slurry density, gas introduction, for example via spargers, not shown for clarity.

Zone A-2: 3-phasic domain: Presence of solid (catalyst particles), gas phase (for example air as oxidation medium), liquid; reaction zone with approximately homogeneous distribution of catalyst particles and virtually constant slurry density; zone A-2 has a relatively low suspension density of solids particles compared to zone A1 as a result of reduced stirrer effect. The oxygen concentration is likewise reduced compared to zone A-1.

Zone A-3: Transition zone: 3-phasic domain: Presence of solid (catalyst particles), gas phase (for example air as oxidation medium), liquid; 3-phasic. mixture partially enters region of zone B, oxygen-depleted gas enters gas space (zone A4) at interface. Zone A-3 exhibits a lower suspension density of solids particles compared to zones A1 and A2 as a result of reduced stirrer effect. Measurable gradient between suspension density A-1 to A-3. Proportion of fine particles markedly increases from bottom to top (from A-1→A3).

Zone A-4: Gas space; particle-free, consists of oxygen-depleted air, oxygen content 4% by vol (+/−3% by vol), gas space is subjected from above to a trickle flow of condensate (contains stabilizer) from the partial coolers.

Zone B-1: Transition to lamella pack, 3-phasic domain (top), distribution and uniformization of flow, biphasic suspension with relatively high density compared to A-1 to A-3 flows downward, gas separation function. Zone B-1 and internals prevent funnel and vortex formation in zone B-2.

Zone B-2: Further gas separation zone and feed to the downcomer (zone B-3), acceleration of flow; at lower portion of zone B-2 the mixture is gas-free to ensure the functioning of the inclined settler. In the case of pressurized operation (1-20 bar) the gases are dissolved and not present physically as gas bubbles. Mixture is now biphasic (liquid and solids particles).

Zone B-3: Downcomer, biphasic suspension with vertically downward flow. Transition zone and discharging of biphasic substreams into individual inclined settler elements of zone C. Vertical velocity greater than in sedimentation zone C-1.

Zone C-1: Entry into lamella and inclined settler elements. Uniformization and retardation of flow. Separation of the solids particles from reaction liquid. Laminar flow profile. Configuration features for loading of lamella pack: 0.05 to 1.5 m3 of liquid per m2 of projected area of inclined settler, optimally 0.3 to 0.7

Zone C-2: Perforated plate and resistance elements at outlet of individual inclined settler elements; configuration features 0.1% to 2% hole area or general outlet area relative to the cross section of a lamella profile, optimally 0.2% to 1%. Smaller perforated plate areas result in polymeric blockages in the apparatus after prolonged continuous operation. Larger perforated plate areas result in short circuit and recirculating streams in the apparatus.

Zone C-3 collection chamber for low-particle or particle-free reaction solution. The reaction solution is under pressure and contains physically dissolved gas constituents. Before being sent for workup (rectification or extraction) the solution is decompressed and very largely degassed. This function has not been shown for clarity.

(a) particle-containing suspension
(b) particle-free liquid
(c) gas bubbles

EXPERIMENTAL

Methacrolein was produced according to U.S. Pat. No. 4,496,770. However, alternative procedures may also be used, as for example in U.S. Pat. No. 9,580,374. According to the prior art methacrolein may in principle be produced starting from propionaldehyde with formalin or by gas phase oxidation of isobutylene with air over a heterogeneous catalyst. The methacrolein qualities obtained after workup are in principle and in the context of the present invention usable as a substrate for direct oxidative esterification in the presence of oxygen-containing gases and methanol to afford MMA.

Example 1 Production of a Pulverulent, Abrasion-Resistant $SiO_2$—$Al_2O_3$—MgO Support Material An enamel-lined receiver was initially charged with 21.36 kg of $Mg(NO_3)_2*6H_2O$ and 31.21 kg of $Al(NO_3)_3*9H_2O$ and the mixture was dissolved in 41.85 kg of DM water while stirring with an impeller stirrer. Thereafter, 1.57 kg of 60% $HNO_3$ were added while stirring.

166.67 kg of silica sol (Köstrosol 1530AS from Bad Köstritz, 30% by weight $SiO_2$, average particle size: 15 nm) were initially charged in an enamel-lined 500 L reactor and cooled to 15° C. while stirring with an impeller stirrer. 2.57 kg of 60% $HNO_3$ were slowly added to the sol while stirring; addition of nitrate solution to the sol from the receiver was carried out over 45 min while stirring. After the addition, the mixture was heated to 65° C. over 30 min and held at this temperature for a further 24 hours, the mixture undergoing gelation and homogeneous commixing being ensured.

After this time the gelated mixture was continuously pumped into a spray dryer as a stirred suspension and subjected to spray drying at an outlet temperature of the laden drying gas of 130° C. The dried green product (the primary product obtained after spray drying) was calcinated twice in a rotary kiln, wherein the residence time in the hot zone (600° C.) was about 45 minutes in each case. The residence time and cycle time of the calcination in the rotary kiln was controlled via the inclination of the rotary kiln (about 1° to 2° inclination). The nitrous gases occurring during the calcination operation were removed in gaseous form and appropriately treated by absorption and chemisorption. The nitrate content in the finished support particles was less than 1000 ppm.

After calcination, 55 kg of a white, flowable pulverulent support material were obtained. The mass yield was about 95%. The spherical support had an average particle size distribution of about 60 μm which was determined by light scattering (Coulter method). The support was subsequently subjected to classification by sieving with several passes and various sieve sizes, wherein the fractions above 120 μm and below 15 μm were removed to the greatest possible extent. Due to technical limitations a fines fraction of about 3.6% by volume remained, i.e. particles which despite sifting had a particle size of between 1 and 15 μm. The yield of the classification step (sifting/sieving) was about 85% and the obtained average particle size distribution of the finished support material was about 68 μm.

Example 2: Production of a Nanoparticulate Gold-Containing Catalyst for Continuous Performance of a Direct Oxidative Esterification of Methacrolein to Afford MMA In an enamel-lined reactor 15 kg of the support were suspended in 50 kg of DM water while stirring with an impeller stirrer. The resulting mixture was heated to 90° C. and aged for 30 minutes after attaining 90° C., A solution of 852.9 g of $Co(NO_3)_2*6H_2O$ in 7.5 kg of DM water was metered in over 10 minutes and the mixture was aged for 30 minutes. 3.7 L of a one molar NaOH solution were subsequently added over 10 minutes. Immediately thereafter, a solution of 376.8 g of auric acid (41% gold) in 7.5 kg of DM water was added and the mixture was aged for 30 minutes. The resulting suspension was cooled to 40° C. and filtered using a centrifuge. The filtercake was washed in the centrifuge with DM water until the filtrate became clear and had a conductivity below 100 μS/cm.

The wet catalyst was dried at 105° C. until the residual moisture was below 5%. The dried catalyst was calcinated in a rotary kiln, wherein the residence time in the hot zone (450° C.) was about 45 minutes. The mass yield was about 99%.

The calcinated catalyst was analysed by SEM-(EDX) and laser diffraction which revealed a spherical eggshell catalyst having an average particle size distribution of about 68 μm. The fines fraction was about 3.5% by volume. ICP revealed a gold content of 0.85% by weight.

The catalyst was employed in this form in the continuous oxidative esterification of methacrolein to afford MMA in example 3.

Example 3

Continuous Performance of a Direct Oxidative Esterification of Methacrolein to Afford MMA I. Reactor, Reaction System and Catalyst Retaining System A stirred tank reactor fitted with a stirrer was used for the reaction. The employed materials are of conventional stainless steel to withstand the slightly corrosive media. The reactor comprises a double shell which is connected to a thermostat which can in turn effect cooling and heating via its medium. The reactor lid is connected to a condenser via a vapour tube (100 mm nominal width).

The stirred tank has an inner diameter of 400 mm and the reactor height up to the lid is 1500 mm. The stirrer is connected to the reactor from below via the floor and is fitted with special stirring means which allow both optimal gas dispersion for the oxygen-containing gas (here compressed air) and optimal suspension of the particulate catalyst in the medium.

A commercial stirrer system consisting of a primary disperser for large gas quantities (Ekato Phasejet) for gas-liquid mixtures having a radial conveying direction and a Combijet stirring means, i.e. two stirring means, secured to the stirrer shaft. The distance of the stirring means from the bottom of the reactor was 100 mm and 400 mm for the second stirring means. The gas conduit for supplying the oxygen-containing gas terminates directly below the dispersion means (distance of gas outlet from dispersing element 10 mm) and ensures uniform distribution of the gas over the reactor cross section and fine dispersion of the oxidation gas.

Above the reactor lid, feed conduits for reactants, recycle streams and auxiliaries are installed in the reactor in such a way that the feed conduits terminate well below the media fill level. The top of the reactor is connected via a conduit with a receiver vessel which contains a methanolic stabilizer solution (1000 ppm Tempol).

Stirrer specifications: Ekato Phasejet consisting of a dispersing element and 6 ">"-shaped blades: Diameter: 0.15 m, 150 mm, Newton number in ungasified model system for the calculation is 1.3 (dimensionless number). The Newton constant for the Phasejet was determined in the model system and derived from Klaus Himmler, Wilfried F. Schierholz, Chemie Ingenieurtechnik 2004, 76, 3, pages 212-219.

In the upper portion of the reactor is a funnel-shaped zone or inlet region which passes the reaction suspension into the internally installed inclined settler. The slurry is initially degassed in the degassing vessel (internal diameter 200 mm with conical lower outflow) so that only dissolved gas constituents remain in the slurry suspension. The lower portion of the degassing vessel is connected to a pipeline having a 30 mm internal diameter and constitutes the upper portion of the downcomer. The now degassed, only biphasic suspension thus flows vertically downward to a Y-shaped branching. The right-hand portion of the branching passes the suspension to the inclined settler element where the biphasic system undergoes efficient sedimentation. The catalyst thus returns to the reactor. At the outlet of the inclined settler is a pressure-resistant sightglass to allow visual examination of the quality of the separation as well as a pressure maintenance means and a valve to control the removal amount. Installed downstream of the pressure valve are two parallel filters made of polypropylene which allow a maximum separation performance of 1 μm (according to manufacturer specifications). The filters are continuously traversed and also integrated via a three way valve such that it is possible for only one filter to be traversed while the other may be changed during ongoing operation.

The lamella elements of the inclined settler are cuboidal four-edged profiles made of stainless steel having internal dimensions of: L=700 mm, H=20 mm, W=50 mm. The usable internal volume is thus 700 mL. A total of 8 lamella elements are installed.

II. Commencement of Reaction and Continuous Reaction:

The reactor was charged with a mixture of methanol, water and MMA, methacrylic acid, as well as dissolved Na methacrylate. Initial charging of this reaction mixture results in faster attainment of the steady-state concentrations. The reactor was charged with 130 kg of this starting medium having a composition of 1.0% to 1.5% by weight of methacrylic acid, wherein 50% thereof was in the form of the sodium salt, 33% by weight of MMA, 5% by weight of water and the rest is methanol. The fill level was about 80-85% of the fill height of the reactor. The reactor was additionally charged with 13 kg of the catalyst according to example 2. The slurry density was thus 10% by weight. The reaction mixture was heated to 80° C. and the stirrer was set to 300 rpm, thus resulting in a specific energy input of about 0.1 kW/m$^3$. The reactor was brought to an operating pressure of 5 bar absolute (using nitrogen as the starting medium). After attaining the reaction temperature the metered addition of methacrolein was commenced (140 mol of MAL per hour) and air was introduced in steps of 1 kg/h, thus causing immediate onset of the reaction as apparent from the fall of the methacrolein level in the reactor and the increase in the MMA concentration in the reaction mixture. The amount of air is adjusted such that the offgas has an oxygen concentration of 4% by volume. The offgas is cooled to −20° C. and the condensate is recycled to the reactor. The residual organics in the offgas account for less than 1.5% by volume and are subjected to thermal treatment.

For steady-state operation methacrolein and methanol are supplied such that the molar ratio of fresh alcohol to aldehyde is 4. A total of 140 moles of methacrolein per hour are introduced into the reactor.

The discharge of the steady-state reaction mixture via the catalyst retaining system (inclined settler and filtration units) is controlled via a pressure valve and is on average 32.5 kg/h. This corresponds to an average reaction time of about 4 h. The ratio of the discharged volume to the volume of the inclined settler element may be calculated as a defined parameter especially for the quality of the solid separation. In the present example this ratio is about 4.06 kg of liquid per lamella element (700 mL) per hour. The volume flow and the cross section of the lamella element may be used to calculate a flow rate of the suspension. If the time for descent of the particles to the lamella floor is calculated to be shorter than the time for traversing the lamella element this results in the catalyst particle being separated/retained. Characteristic therefor are not only the volume flow but also the rate of descent of the catalyst particles which in turn depends on the density difference of the medium and the catalyst particles and the catalyst diameter. To describe inclined settler loading, the volume flow of the liquid is divided by the projected lamella area; this results in a loading in m$^3$/m$^2$×h, i.e. m/h. In the present example this parameter is about 0.14 m³/m²×h (density of 800 kg/m³, lamella area 700 mm×50 mm, projected area scaled with the angle of inclination of 60°).

The reaction mixture is decompressed and passed into a column via an intermediate vessel having a volume of 10 L. In this so-called methacrolein-methanol recovery column (operating pressure 1 bar absolute) the methacrolein not converted in the reaction and excess methanol are condensed overhead and recycled into the reactor.

The bottoms product contains crude MMA having MAL contents of less than 1000 ppm and the higher-boiling byproducts of the reaction, in particular methyl methoxy-isobutyrate (MMIB) and methacrylic acid (MAA). The crude MMA may then be purified to afford MMA of commercial quality and purity.

In the steady state a conversion rate between 70% and 72% is established and the selectivity of the reaction is on average 94.4% for MMA, 3.0% for methacrylic acid and 1.2% for MMIB, wherein the respective reference value is the amount of the employed methacrolein, Including the losses of the reactants (methacrolein) and MMA, in the offgas the C4 balance is virtually 100%.

The evolution of conversion and selectivity over a running time of the plant of nearly 1000 operating hours is shown in FIG. 1. The conversion and selectivity also remain unchanged when continuing long-term continuous operation over a total time of more than 9000 h (but are not shown for clarity). The catalyst was regularly removed during ongoing operation via a bypass conduit. The particle size spectrum was determined from the removed catalyst slurry samples to analyse the intactness of the catalyst system. FIG. 2 shows micrographs of the catalyst samples and particle size analyses at various operating junctures. "0 h" represents fresh catalyst. It is apparent that in the case of operation according to the invention the catalyst remains mechanically intact, even over an operating time of more than 9000 hours.

According to the invention the classification in the inclined settler leads to a reduction in catalyst present in the reactor over the first almost 100 hours of operating time, with the result that the conversion of methacrolein falls. The selectivities for MMA and MMIB are unaffected, unlike the selectivities for MAA and methyl isobutyrate. The reason for this is on the one hand the discharging of—more active—fines fraction which generates more methyl isobutyrate and on the other hand for MAA a delayed change in the water content in the reaction matrix which results in a change in the selectivity for MAA as shown in FIG. 3. A fall in the selectivity for methyl formate surprisingly also results, also shown in FIG. 3. This has several advantages such as reduced hydrolysis to form formic acid, thus causing the NaOH demand of the reaction to fall, and reduced amounts of methyl formate in the offgas stream. Methyl formate can react with water from the offgas at the condensation site to form formic acid and methanol, thus increasing the corrosivity of the offgas condensate.

The reactor discharge from the above-described continuous reaction was sampled at regular intervals and the amount of catalyst exiting the inclined settler and present therein was determined. To this end the sample of reaction medium was filtered through a 1 μm depth filter and the residue determined gravimetrically after drying. Immediately after commencement the suspension still has a concentration of about 1200 ppm of catalyst. This is apparent inter alia from the slight purple colouring of the suspension. The catalyst concentration rapidly decreased and after about 20 reactor volumes of discharge, corresponding to a reaction time of 80 to 100 hours, reached an asymptotic minimum of about 1 ppm. Sampling was then stopped.

The catalyst of the last sample was homogenized and analysed in terms of its particle size distribution by the Coulter method and showed no change from the previous state.

The classifying effect which ensures that only very small residual particles are discharged via the inclined settler is observable according to the invention. This conforms with the stable conversion function after almost 100 hours. It was therefore demonstrated that over a short operating time of just a few days the disruptive fines fraction of the fresh catalyst is discharged from the reactor effectively and in a classifying manner by the present inventive reactor and catalyst retaining system, that this discharge can be recovered to the greatest possible extent and subsequently recycled with a fine filter, and that after this startup and conditioning phase the conversion and the steady-state reaction concentration remain stable, thus allowing problem-free operation of the workup portion without substantial adaptation of the operating parameters.

Examples 4 a-f

The examples show experimentally the effects of power input and specific power input on the reaction rate and the effect of the two parameters on the abrasion resistance of the catalyst under reaction conditions.

In a 20 L stirred tank reactor having an internal free diameter of 200 mm, the reaction was performed with reaction parameters from example 3 and catalyst from example 2. The reactor content during the experiments was a stable 13 l (+/−2%) with the composition as indicated in example 3.

Reactor 4 was fitted with baffles (width: 20 mm) to prevent formation of a funnel by the stirrer and ensure an approximately uniform surface of the gasified reaction matrix.

An Ekato Phasejet stirrer (from the Ekato catalogue) having a diameter of 120 mm and 6 stirrer blades was installed. A portion of the reaction solution was removed via a filter candle system with a mixture, adjusted to pH 8.5 with a solution of methanol/water and sodium hydroxide solution and returned to the reactor for stable control of the pH in the reactor at pH 7.

To calculate the specific power input a literature value of 1.3 was used as the Newton number of the Phasejet and the Reynolds number was determined.

The stirrer speed was varied and in this regard the corresponding performance data of the stirrer were ascertained and calculated according to the stirrer speed. The results are reported in the following table:

TABLE 1

| Experiment number | Stirrer speed [RPM] | Stirrer speed [sec-1] | Reynolds number | Orbital velocity [m/s] | Spec. energy input [kW/m$^3$] | Residual O2 in offgas [% by vol.] |
|---|---|---|---|---|---|---|
| V4-a | 375 | 6.25 | 171439 | 2.36 | 0.47 | 4.6 |
| V4-b | 400 | 6.67 | 182868 | 2.51 | 0.58 | 4.4 |
| V4-c | 475 | 7.92 | 217156 | 2.98 | 0.96 | 4.2 |
| V4-d | 550 | 9.17 | 251444 | 3.46 | 1.50 | 4.0 |
| V4e | 600 | 10.00 | 274302 | 3.77 | 1.94 | 4.0 |
| V4-f | 700 | 11.67 | 320020 | 4.40 | 3.09 | 4.0 |

These correlations between stirrer speed/orbital velocity of the stirrer and the resulting residual oxygen content in the emission gas are shown in FIG. 4. As a measure for the orbital velocity, the so-called tip speed was determined here, i.e. the orbital velocity of the stirrer at the outer stirrer blade tip. It can be derived that falling below a particular stirrer speed causes the space-time yield of the reaction to decrease, as is apparent from the increasing residual oxygen amount in the offgas. In this regime the reaction is performable without limitations as before, however in this regime there is a limitation on the space time yield as a consequence of limited gas diffusion, i.e. the residence time in the gas bubbles is no longer sufficient in this experimental set up.

Comparative Example 4 g

In example 4 g a continuous reaction according to the described set up 4 a-f was performed.

The power input via the stirrer was established at a stirrer speed which corresponds to a comparatively high specific power input >3 kW per cubic meter of reaction solution. The reaction was operated at steady-state conversions and a constant composition of the reaction matrix and the reaction was operated over 500 h, a reaction sample being removed at 100 h intervals to assess catalyst abrasion and the intactness of the catalyst powder. The results of the experiments are reported in the following table:

As a consequence of the high specific power input, average particle diameter decreases with increasing experimental duration. Simultaneously the measured proportion of fine particles (specified arbitrarily as particles having a diameter of less than 20 μm) in the reactor increases continuously. The experiment was aborted since towards the end of the experimental duration, after 500 h, the filter system suffered repeated blockages that were only removeable by repeated percussive backwashing with reactor liquid. The fall in the average particle diameter/the increasing amount of fines fraction is shown in FIGS. 5A and 5B.

Example 5

An execution as in examples 4 was chosen. The experimental settings were operated for different durations.

The average particle diameter of the catalyst suspension and the fines fraction (number of particles in the reactor having a diameter smaller than 20 μm) were determined at different durations of the respective settings.

TABLE 2

| Experiment number | Stirrer speed [RPM] | Stirrer speed [sec-1] | Spec. energy input [kW/m$^3$] | Residual O2 in offgas [% by vol.] | Running time [h] | Average particle diameter (d50) [μm] | Fines fraction <20 μm [% by vol.] |
|---|---|---|---|---|---|---|---|
| V4-g | 700 | 11.67 | 3.09 | 4.0 | 0 | 75.1 | 1.6 |
| V4-g | 700 | 11.67 | 3.09 | 4.0 | 100 | 70.2 | 2.78 |
| V4-g | 700 | 11.67 | 3.09 | 4.0 | 200 | 67.3 | 4.23 |
| V4-g | 700 | 11.67 | 3.09 | 4.0 | 300 | 62.3 | 5.18 |
| V4-g | 700 | 11.67 | 3.09 | 4.0 | 400 | 56.3 | 6.55 |
| V4-g | 700 | 11.67 | 3.09 | 4.0 | 500 | 51.2 | 7.83 |

TABLE 3

| Experiment number | Stirrer speed [RPM] | Stirrer speed [sec-1] | Spec. energy input [kW/m³] | Residual O2 in offgas [% by vol.] | Running time [h] | Average particle diameter (d50) [μm] | Fines fraction <20 μm [% by vol.] |
|---|---|---|---|---|---|---|---|
| V5 -a | 375 | 6.25 | 0.47 | 4.6 | 0 | 75.1 | 1.60 |
|  | 375 | 6.25 | 0.47 | 4.6 | 500 | 75.0 | 1.59 |
|  | 375 | 6.25 | 0.47 | 4.6 | 1000 | 75.1 | 1.58 |
| V5-b | 400 | 6.67 | 0.58 | 4.4 | 500 | 75.0 | 1.60 |
| V5-c | 475 | 7.92 | 0.96 | 4.2 | 500 | 74.9 | 1.62 |
| V5-d | 550 | 9.17 | 1.50 | 4.0 | 500 | 74.2 | 1.61 |
| V5-e | 600 | 10.00 | 1.94 | 4.0 | 500 | 72.0 | 2.48 |
| V5-f Comparative example | 650 | 10.83 | 2.47 | 4.0 | 500 | 64.8 | 4.21 |
| V5-g, Comparative example | 700 | 11.67 | 3.09 | 4.0 | 500 | 51.2 | 7.83 |

It is apparent from the table that at low power inputs the average particle diameter of the catalyst is unchanged at operating times up to 100 h, the same applying to the proportion of the fine particles. At power inputs up to 2 kW/m3 the abrasion of the catalyst particles is not present, markedly reduced or low.

In comparative examples V5f and V5-g abrasion is comparatively high as is apparent from the low average particle diameter after 500 h. For the comparative examples the gold content was determined by ICP (see ex. 2: production of Au-containing catalyst: gold content at 0° C. operating time measured immediately after catalyst synthesis; 0.85% by weight).

After a synthesis time of 500 h and 1000 h a reactor sample of experiment V5-a was removed and the Au content determined by ICP analysis. A gold concentration of 0.84% by weight was determined by duplicate determination after 500 h and also after 1000 h. The minimal decrease in the gold content indicates that abrasion of the catalyst is minimal. The minimal reduction in the content found may be explained by the minimal discharge of fines fractions from the reactor system. Inspection of the reactor, stirrer and filter candles after the experiment had ended revealed no deposits.

After a synthesis time of 500 h in the comparative experiments respective reactor samples were removed and the Au content determined by ICP analysis. In example V5-g a gold value of 0.76% by weight was determined by duplicate determination.

In example V5-f a gold value of 0.60% by weight was determined by duplicate determination after a synthesis time of 500 hours.

The relatively clear reduction in the gold content after 500 h indicates that abrasion of the catalyst is significant. The reduction in the content found clearly correlates with the specific power input via the stirrer. Inspection of the reactor, stirrer and filter candles after the experiment had ended revealed gold deposits on the stirrer, in particular on the stirrer blades and the dispersing element.

Attached FIG. 6 shows a graphic representation of this correlation and the results.

Example 6 a. Inventive: with internals in zone B-1 for flow calming and degassing of the mixture entering zone C
b. Comparative example: without internals in zone B-1 for flow calming and degassing of the mixture entering zone C In example 6 an experimental setup and reactor according to the setup in example 3 was chosen. In a departure therefrom, a stirrer system comprising three Ekato Combijet stirrers having a diameter of 150 mm and installed on one shaft was chosen. One stirrer consists of a plurality of stirrer blades and installation took into account the offset of the stirrer blades in order to minimize vibrations and ensure smooth running. For calculation of the specific power input a Newton number of 0.7 was assumed. Compared to example 1 the power input is thus markedly reduced. A gas introduction ring (sparger) comprising 10 holes was installed below the lower Combijet stirrer blade to ensure air introduction and gas dispersion. The sparger had a diameter of 120 mm.

The stirrer speed was adjusted such that the specific power input according to the formula was 0.1 kW/m3 of reaction liquid. As a constant reaction volume of about 130 kg a discharge of 75 kg/h from the reactor was established. At the reactor outlet, downstream of the inclined settler outlet and upstream of the secondary depth filters, the filtrate was passed through a turbidity measurement means to allow optical quantification of the solids content.

Each of the lamella profiles (8 rectangular profiles, each of 700 mm in length, 20 mm in height and 50 mm in width) were provided at the lamella outlet with a fine hole having a radius of 0.95 mm corresponding to a 0.3% outlet hole area relative to a 1000 m² profile cross-sectional area.

A catalyst according to example 2 was charged and a catalyst fraction of 15% by weight, i.e. 20.5 kg of catalyst powder at a steady-state reactor fill level of 130 kg (~150 L volume) was used. The conical feed portion in zone B, in which the reaction mixture is diverted, is provided in the upper portion with flow tubes of 20 cm in length (height, width, length=200 mm, 20 mm, 20 mm). The mode of operation and configuration were analysed by CFD simulation to ensure that the downwards flow in zone B-1 is markedly slower than the ascent velocity of the gas bubbles. This ensures that the downcomer (Zone 8-3) is supplied from above with a biphasic suspension. The biphasic suspension is more or less free from gas bubbles and consists of the steady-state reaction solution, which contains only dissolved gas constituents, and the heterogeneous catalyst. In zone B-3 (the downcomer) the tube elements of the inclined settler are supplied with suspension. The fines fraction of the freshly employed catalyst was 3.5% by volume of particles according to analysis of the particle size spectrum with an average diameter of smaller than 20 μm, of which 1.0% by volume were smaller than 10 μm.

Result 6a:
After 150 h: The reactor discharge measured by turbidity measurement at the outlet of the reactor and lamella pack fell over the first 150 h from initially about 700 ppm of catalyst discharge to 1-2 ppm (corresponding to less than 0.5 g of catalyst/h of discharge after 150 h of operating time).

MMA selectivity: 95.2%, MAL conversion: 72%

The 1 ppm depth filters needed to be switched over three times over this period. After a workup of the filter 123 g of fine catalyst material were recovered and sent for noble metal workup.

After 150 h the reactor sample had a fines fraction of particles smaller than 20 µm of <1% by weight (based on the total solids fraction in the suspension sample), the remaining proportion of particles was below 0.1% by weight.

After 700 h: The reactor discharge measured by turbidity measurement at the outlet of the reactor and lamella pack fell to about 1 ppm over a reaction time of 500 h (corresponding to less than 0.2 g of catalyst/h discharge which corresponds to the accuracy and reliability of the turbidity measurement). Removed samples showed no sedimentation or deposition of solids after a resting time of 20 min which indicates ultrafine particles/that the samples are free from particles.

MMA selectivity: 95.2%, MAL conversion: 71%

The 1 ppm depth filters needed to be switched over once during this period. After a workup of the filter, 53 g of fine catalyst material were recovered and sent for noble metal workup.

After 700 h the reactor sample had a fines fraction of particles smaller than 20 µm of <0.2% by weight (based on the total solids fraction in the suspension sample), the remaining proportion of particles below 10 µm was below the limit of detection.

After 3000 h: Unchanged selectivity and conversion as after 700 h.

The 1 ppm depth filters needed to be switched over once during this period. After a workup of the filter 15 g of fine catalyst material were recovered and sent for noble metal workup.

After 3000 h the reactor sample had a fines fraction of particles smaller than 20 µm of <0.1% by weight (based on the total solids fraction in the suspension sample), the remaining proportion of particles below 10 µm was below the limit of detection.

Conclusion: The long-term experiment 6a, over an experimental duration of 3000 h shows
a.) stable long-term operation in the inventive embodiment and shows
b.) that fines fractions from catalyst manufacture (in the case of incomplete sifting) may be separated and recovered effectively,
c.) that the low power input into the reaction system allows abrasion of the catalyst to be effectively minimized/prevented without a reduction in catalyst performance or space-time yield.

For 6b, the experiment was repeated analogously but without the internals in zone B-1. The reaction proceeded normally over the first 150 hours of conversion and selectivity, but a decline was subsequently observed. This coincided with the approximately 5 to 10 times greater amount of solids discharge/solids passage through the inclined settler. After about 700 hours 11% of the catalyst amount had been eluted from the reactor. The experiment was operable in principle but would not have been economically and safely operable on a long-term basis in this form. CFD simulation confirmed an irregular flow profile in the lamellae and an elongated inlet zone in the lamellae, thus reducing the separation/settling area.

The invention claimed is:

1. A process for producing alkyl methacrylates, comprising:
    reacting methacrolein with an alkyl alcohol in the presence of an oxygen-containing gas and a particulate, pulverulent catalyst in a liquid phase, in a reaction mixture in a reactor, to obtain an alkyl methacrylate;
    wherein the reactor comprises a zone A, at least one zone B-1, at least one zone B-2, a zone B-3, and at least one zone C, and
    wherein
    zone A represents a primary reaction zone and is provided with at least one stirring means for intensive commixing of gaseous, liquid, and solid phases in zone A,
    the at least one zone B-1 is provided with internals for flow calming which very largely prevent entry of the gaseous phase into subsequent zones of the at least one zone B-2, zone B-3, and the at least one zone C,
    zone B-3 contains the reaction mixture which has been very largely freed of the gaseous phase and is connected to the at least one zone C,
    the at least one zone C comprises a continuously classifying sedimentation apparatus, wherein an average vertical flow in zone A and the at least one zone C is upwards, and an average vertical flow in the at least one zone B-1, the at least one zone B-2, and zone B-3 is downwards, and
    an energy input for suspension of the catalyst by the at least one stirring means is limited to not more than 3 kilowatts per cubic meter of the reaction mixture.

2. The process according to claim 1, wherein a portion of the reaction mixture from the at least one zone B-2 enters the at least one zone C,
    wherein the catalyst is separated in the sedimentation apparatus into a first fraction of relatively small catalyst particles, at least 60% by weight of which have a diameter of less than 20 µm, and a second fraction of remaining catalyst particles, which are on average relatively large, and
    wherein the first fraction exits the reactor with the reaction mixture at an outlet of the at least one zone C, and wherein a concentration of discharged catalyst particles in the reaction mixture is between 1 and 200 ppmw.

3. The process according to claim 1, wherein an energy input for suspension of the catalyst and for gas dispersion by the at least one stirring means is limited to 0.05 to 1.0 kW per cubic meter of the reaction mixture.

4. The process according to claim 1, wherein zone A comprises a zone A-1 and a triphasic zone A-2 or triphasic zone A-3, which is arranged above the zone A-1 and does not have the at least one stirring means, and
    wherein no gas bubble dispersion is brought about by an effect of the at least one stirring means.

5. The process according to claim 1, wherein the alkyl alcohol is methanol and the alkyl methacrylate is methyl methacrylate (MMA).

6. The process according to claim 1, wherein the reactor has a ratio of diameter to height of a gasified fluid level between 1:1 and 1:50.

7. The process according to claim 1, wherein at a transition of zone A to the at least one zone B-1, the internals are present which effect flow uniformization of the reaction mixture upon entry into the at least one zone B-1.

8. The process according to claim 1, wherein a ratio of a volume of zone A to a total volume of the at least one zone B-1, the at least one zone B-2, zone B-3, and the at least one zone C is greater than 1 and less than 500.

9. The process according to claim 1, wherein the reactor has one or more feed conduits through which a mixture may be added, the mixture comprising the alkyl alcohol, MMA, the methacrolein, water, and optionally, dissolved alkali metal salts of methacrylic acid, and wherein the one or more feed conduits may optionally be distributed over a vertical height of the reactor.

10. The process according to claim 1, wherein the sedimentation apparatus consists of a plurality of channel-like profiles, tubes, or lamellae having an angle of inclination to a horizontal.

11. The process according to claim 10, wherein the plurality of channel-like profiles, tubes, or lamellae have identical pressure at an inlet.

12. The process according to claim 1, wherein the sedimentation apparatus is an inclined settler or a hydrocyclone.

13. The process according to claim 2, wherein the second fraction of remaining catalyst particles is retained in the sedimentation apparatus in the at least one zone C and is recycled into zone B-3, and wherein the first fraction of relatively small catalyst particles are collected using a filter system.

14. The process according to claim 1, wherein zone A in a lower portion of the reactor is actively supplied with the oxygen-containing gas via nozzles or gasification apparatuses, and wherein the at least one zone B-1, the at least one zone B-2, and zone B-3 do not comprise any apparatuses for active gasification of the reaction mixture.

15. The process according to claim 1, wherein zone A is separated from the at least one zone B-1, the at least one zone B-2, and zone B-3 by dividing walls.

16. The process according to claim 1, wherein the internals at the transition of zone A to the at least one zone B-1 largely prevent entry of gas bubbles into the at least one zone B-1, the at least one zone B-2, and zone B-3.

17. The process according to claim 1, wherein an average catalyst particle diameter of the catalyst is between 20 and 120 µm.

18. The process according to claim 13, wherein the filter system comprises at least two successively traversed filters downstream of elements of the at least one zone C, wherein a first filter of the at least two successively traversed filters collects coarse particles having a diameter greater than 5 µm, and a second filter of the at least two successively traversed filters collects fine particles having a diameter greater than 0.1 µm.

19. The process according to claim 1, wherein zone A comprises a zone A-1, a zone A-2, and a zone A-3, and wherein zone A-2 and zone A-3 are separated by dividing walls from the at least one zone B-2 and zone B-3.

20. The process according to claim 1, wherein zone A comprises a zone A-1, a zone A-2, and a zone A-3, and wherein internals at a transition of zone A-2 and zone A-3 to the at least one zone B-1 largely prevent entry of gas bubbles into the at least one zone B-1, the at least one zone B-2, and zone B-3.

* * * * *